United States Patent
Cawthon

(10) Patent No.: US 9,169,516 B2
(45) Date of Patent: Oct. 27, 2015

(54) METHODS OF PREDICTING MORTALITY RISK BY DETERMINING TELOMERE LENGTH

(75) Inventor: Richard Cawthon, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 567 days.

(21) Appl. No.: 10/543,111

(22) PCT Filed: Jan. 26, 2004

(86) PCT No.: PCT/US2004/002215

§ 371 (c)(1),
(2), (4) Date: Mar. 10, 2006

(87) PCT Pub. No.: WO2004/068110

PCT Pub. Date: Aug. 12, 2004

(65) Prior Publication Data

US 2006/0210980 A1    Sep. 21, 2006

Related U.S. Application Data

(60) Provisional application No. 60/442,456, filed on Jan. 24, 2003.

(51) Int. Cl.
*C12Q 1/68* (2006.01)
*C12P 19/34* (2006.01)

(52) U.S. Cl.
CPC ............ *C12Q 1/6883* (2013.01); *C12Q 1/6886* (2013.01); *C12Q 2600/118* (2013.01)

(58) Field of Classification Search
None
See application file for complete search history.

(56) References Cited

U.S. PATENT DOCUMENTS

| | | | | |
|---|---|---|---|---|
| 5,489,508 | A * | 2/1996 | West et al. | 435/6 |
| 5,686,245 | A | 11/1997 | West | 435/6 |
| 5,741,677 | A | 4/1998 | Kozlowski | 435/91.2 |
| 5,741,678 | A | 4/1998 | Ronai | 435/912 |
| 5,834,193 | A | 11/1998 | Kozlowski et al. | |
| 5,856,096 | A | 1/1999 | Windle et al. | |
| 6,020,124 | A | 2/2000 | Sorenson | 435/6 |
| 6,436,677 | B1 | 8/2002 | Gu | 435/183 |
| 7,695,904 | B2 | 4/2010 | Cawthon | 435/6 |
| 8,048,631 | B2 | 11/2011 | Cawthon | 435/6.12 |
| 2003/0162266 | A1 | 8/2003 | Cawthon | 435/6 |
| 2006/0210980 | A1 | 9/2006 | Cawthon | 435/6 |
| 2011/0207128 | A1 | 8/2011 | Cawthon | 435/6 |
| 2011/0294676 | A1 | 12/2011 | Cawthon | 435/6.12 |

FOREIGN PATENT DOCUMENTS

| | | |
|---|---|---|
| AU | 2003208902 | 1/2003 |
| AU | 2009329987 | 7/2010 |
| CA | 2474468 | 1/2003 |
| CA | 2513747 | 1/2004 |
| CA | 2748265 | 7/2010 |
| CN | 03804867.1 | 1/2003 |
| CN | 200980157269.8 | 7/2010 |
| DE | 03707624.7 | 1/2003 |
| EP | 03707624.7 | 1/2003 |
| EP | 04705326.9 | 1/2004 |
| EP | 12152681.8 | 1/2004 |
| EP | 09804177.5 | 7/2010 |
| ES | 03707624.7 | 1/2003 |
| FR | 03707624.7 | 1/2003 |
| GB | 03707624.7 | 1/2003 |
| HK | 05103554.7 | 1/2003 |
| HK | 1169681 | 7/2010 |
| IT | 03707624.7 | 1/2003 |
| JP | 09-206081 A | 8/1997 |
| JP | 2006-564211 | 1/2003 |
| JP | 2006-503063 | 1/2004 |
| JP | 2011-543646 | 7/2010 |
| WO | PCT/US1996/010035 | 12/1996 |
| WO | PCT/JP1999/006711 | 6/2001 |
| WO | PCT/US2001/007101 | 9/2001 |
| WO | PCT/US2003/002844 | 1/2003 |
| WO | WO 2004/068110 | 1/2004 |
| WO | PCT/US2006/013462 | 10/2006 |
| WO | PCT/US2009/069243 | 7/2010 |
| WO | WO 2010/075413 | 7/2010 |

OTHER PUBLICATIONS

Bechter et al., "Telomere Length and Telomerase Activity Precit Survival in Patients with B Cell Chronic Lymphocytic Leukemia," Cancer Research, 1998, vol. 58, pp. 4918-4922.*

Chang et al., "Telomere Length and replicative aging in human vascular tissues," PNAS, USA, 1995, vol. 92, pp. 11190-11194.*

Palmer et al., "Telomere Length, Telomerase Activity, and Replicative Potential in HIV Infection: Analysis of CD4+ and CD8+ T Cells from HIV-discordant Monozygotic Twins," The Journal of Experimental Medicine, Apr. 1997, vol. 185, No. 7, pp. 1381-1386.*

Kim et al., "Specific Association of Human Telomerase Activity with Immortal Cells and Cancer," Science, 1994, vol. 266, pp. 2011-2015.*

Christensen et al. The quest for genetic determinants of human longevity: challenges and insights. Nature Reviews Genetics 7:436-448 (Jun. 2006).*

Harris et al. The association between telomere length, physical health, cognitive ageing, and mortality in non-demented older people. Neuroscience Letters 406:260-264 (2006).*

Bendix et al. Longitudinal changes in leukocyte telomere length and mortality in humans. J Gerontol A Biol Sci Med Sci (2013). (abstract only) retrieved on Jan. 6, 2014 from http://www.ncbi.nlm.nih.gov/pubmed/24149432.*

(Continued)

*Primary Examiner* — Samuel Woolwine
(74) *Attorney, Agent, or Firm* — Ballard Spahr LLP

(57) ABSTRACT

The present invention provides for methods of determining telomere length of an organism and correlating the measured telomere length with mortality risk associated with telomere length in a population. The presence of shorter telomeres is associated with an increased mortality rate and increased susceptibility to certain types of diseases for an individual member of a human population.

10 Claims, 4 Drawing Sheets

(56) References Cited

OTHER PUBLICATIONS

Zekry et al. Telomere length, comorbidity, functional, nutritional and cognitive status as predictors of 5 years post hospital discharge survival in the oldest old. J Nutr Health Aging 16(3):225-30, Mar. 2012) (abstract only) retrieved on Jan. 3, 2014 from http://www.ncbi.nlm.nih.gov/pubmed/22456777.*
Sanders et al. Telomere length in epidemiology: A biomarker of aging, age-related disease, both, or neither? Epidemiologic Reviews 35:112-131 (2013).*
Frenck et al. The rate of telomere sequence loss in human leukocytes varies with age. PNAS 95:5607-5610 (1998).*
Griffith et al., "Mammalian Telomeres End in a Large Duplex Loop," Cell, 97:503-514 (1999).
Munoz-Jordan et al., "t-loops at trypanosome telomeres," EMBO J., 20:579-588 (2001).
Zhang, X., et al., "Telomere shortening and apoptosis in telomerase-inhibited human tumor cells," Genes Dev., 2388-99 (1999).
Rudolph, et al., "Longevity, Stress Response, and Cancer in Aging Telomerase-Deficient Mice," Cell, 96:701-12 (1999).
Herrera, E., et al., "Disease states associated with telomerase deficiency appear earlier in mice with short telomeres," EMBO J, 18:2950-60 (1999).
Cherif, et al., "Ageing and telomeres: a study into organ- and gender-specific telomere shortening," Nucleic Acids Research, 31(5):1576-1583 (2003).
Brummendorf, et al., "Telomere length in leukocyte subpopulations of patients with aplastic anemia," Blood, 97(4):895-900 (2001).
Austriaco, Jr., et al., "Changes of telomere length cause reciprocal changes in the liefspan of mother cells in Saccharomyces cerevisiae," Proc. Natl. Acad. Sci. USA, 94:9768-9772 (1997).
Samani, et al., "Telomere shortening in atherosclerosis," Lancet, 358:472-73 (2001).
Cawthon, "Telomere measurement by quantitative PCR," Nucleic Acids Research, 30:10 e47 2002.
Cawthon, et al., "Association between telomere length in blood and mortality in people aged 60 years or older," Lancet, 361:393-95 (2003).
Almasy L, et al. (1998) Multipoint quantitative-trait linkage analysis in general pedigrees. Am J Hum Genet. 62: 1198-1211.
Bakaysa, S.L. et al. (2007) Telomere length predicts survival independent of genetic influences. Aging Cell. (6): 769-774.
Beekman M, et al. (2006) Chromosome 4q25, microsomal transfer protein gene, and human longevity: novel data and a meta-analysis of association studies. J Gerontol A Biol Sci Med Sci. 61(4): 355-362.
Blasco MA, et al. (1997) Telomere shortening and tumor formation by mouse cells lacking telomerase RNA. Cell. 91(1): 25-34.
Boulay JL, et al. (1999) Gene dosage by quantitative real-time PCR. Biotechniques. 27(2): 228-230, 232.
Brown MD, et al. (2006) IQGAP1 in cellular signaling: bridging the GAP. Trends Cell Biol. 16(5): 242-249.
Cawthon RM, et al. (2003) Association between telomere length in blood and mortality in people aged 60 years or older. Lancet. 361: 393-395.
Cawthon RM. (2002) Telomere measurement by quantitative PCR. Nucleic Acids Res. 30(10): e47.
Cawthon RM. (2009) Telomere length measurement by a novel monochrome multiplex quantitative PCR method. Nucleic Acids Res. 37(3): e21.
Cheung VG, et al. (2002) The genetics of variation in gene expression. Nat Genet. 32 Suppl: 522-525.
Cheung VG, et al. (2003) Natural variation in human gene expression assessed in lymphoblastoid cells. Nat Genet. 33: 422-425.
Cheung VG, et al. (2005) Mapping determinants of human gene expression by regional and genome-wide association. Nature. 437(7063): 1365-1369.
D'Aquila, R.T. et al. (1991) Maximizing sensitivity and specificity of PCR by pre-amplification heating. Nucleic Acid Research. 19(13): 3749.

Dai M, et al. (2005) Evolving gene/transcript definitions significantly alter the interpretation of GeneChip data. Nucleic Acids Res. 33(20): e175.
Dausset J, et al. (1990) Centre d'etude du polymorphisme humain (CEPH): collaborative genetic mapping of the human genome. Genomics. 6(3): 575-577.
Dixon AL, et al. (2007) A genome-wide association study of global gene expression. Nat Genet. 39(10): 1202-1207.
Don, R.H. et al.(1991) 'Touchdown' PCR to circumvent spurious priming during gene amplification. Nucleic Acid Research. 19(14): 4008.
Dustin ML (2006) Immunology. When F-actin becomes too much of a good thing. Science. 313(5788): 767-768.
Efron B, et al. (2004) Least angle regression. Ann Statist. 32(2): 407-499.
Efron B, et al. (2007) On testing the significance of sets of genes. Ann Appl Stat. 1(1): 107-129.
Ehrlenbach, S. et al. (2009) Influences on the reduction of relative telomere length over 10 years in the population-based Bruneck study: introduction of a well-controlled high-throughput assay. Intl. J. Epidemiol. (38): 1725-1734.
Fitzpatrick, A.L. (2011) et al., Leukocyte telomere length and mortality in the cardiovascular health study. J. Gerontol. A. Biol. Sci. Med. Sci. 66A(4): 421-429.
Foger N, et al. (2006) Requirement for coronin 1 in T lymphocyte trafficking and cellular homeostasis. Science. 313: 839-842.
Frank IE, et al. (1993) A statistical view of some chemometrics regression tools (with discussion). Technometrics. 35: 109-148.
Geesaman BJ, et al. (2003) Haplotype-based identification of a microsomal transfer protein marker associated with the human lifespan. Proc Natl Acad Sci USA. 100(24): 14115-14120.
Goring HH, et al. (2007) Discovery of expression QTLs using large-scale transcriptional profiling in human lymphocytes. Nat Genet. 39(10): 1208-1216.
Hamilton B, et al. (2005) A systematic RNAi screen for longevity genes in C. elegans. Genes Dev. 19(13): 1544-1555.
Haraldsson MK, et al. (2008) The lupus-related Lmb3 locus contains a disease-suppressing Coronin-1A gene mutation. Immunity. 28: 40-51.
Harley CB, et al. (1990) Telomeres shorten during ageing of human fibroblasts. Nature. 345(6274): 458-460.
Henderson, S. et al. (1996) In situ analysis of changes in telomere size during replicative aging and cell transformation. J. Cell Biol. 134(1): 1-12.
Herrera E, et al. (1999) Disease states associated with telomerase deficiency appear earlier in mice with short telomeres. EMBO J. 18(11): 2950-2960.
Higuchi R, et al. (1993) Kinetic PCR analysis: real-time monitoring of DNA amplification reactions. Biotechnology (NY). 11(9): 1026-1030.
Hoerl AE, et al. (2000) Ridge regression: Biased estimation for nonorthogonal problems. Technometrics. 41: 80-86.
Hultdin M, et al. (1998) Telomere analysis by fluorescence in situ hybridization and flow cytometry. Nucleic Acids Res. 26(16): 3651-3656.
Johnson MR, et al. (2000) Quantitation of dihydropyrimidine dehydrogenase expression by real-time reverse transcription polymerase chain reaction. Anal Biochem. 278(2): 175-184.
Kainz P. (2000) The PCR plateau phase—towards an understanding of its limitations. Biochim Biophys Acta. 1494: 23-27.
Kerber RA et al. (2001) Familial excess longevity in Utah genealogies. J Gerontol A Biol Sci Med Sci. 56: B130-139.
Kerber RA, et al. (2009) Gene expression profiles associated with aging and mortality in humans. Aging Cell. 8(3): 239-250.
Kimura, M. et al. (2008) Telomere length and mortality: a study of leukocytes in elderly Danish twins. Am. J. Epidemiol. 167(7): 799-806.
Kuniaki, A. et al. (2002) Two independent regions of human telomerase reverse transcriptase are important for its oligomerization and telomerase activity. J. Biol. Chem. 277(10): 8538-8544.
Kuramoto, M. et al. (2001) Identification and analyses of the Xenopus TERT gene that encodes the catalytic subunit of telomerase. Gene. 277: 101-110.

(56) References Cited

OTHER PUBLICATIONS

Lawyer FC, et al. (1993) High-level expression, purification, and enzymatic characterization of full-length *Thermus aquaticus* DNA polymerase and a truncated form deficient in 5' to 3' exonuclease activity. PCR Methods Appl. 2(4): 275-287.
Li B, et al. (2003) Rap1 affects the length and heterogeneity of human telomeres. Mol Biol Cell. 14(12): 5060-5068.
Liu H, et al. (2007) AffyProbeMiner: a web resource for computing or retrieving accurately redefined Affymetrix probe sets. Bioinformatics. 23: 2385-2390.
Liu WM, et al. (2002) Analysis of high density expression microarrays with signed-rank call algorithms. Bioinformatics. 18(12): 1593-1599.
Loffert, D. et al. (1997) PCR optimization: primer design. Qiagen News. 5: 3-6.
Lunetta KL, et al. (2007) Genetic correlates of longevity and selected age-related phenotypes: a genome-wide association study in the Framingham Study. BMC Med Genet. 8 Suppl 1: S13.
Masaki, Y. et al. (2002) Telomerase activity detected in eyed embryos of rainbow trout *Oncorhynchus mykiss*. Fisheries Science. 68: 132-137.
Mather, K.A. et al. (2010) Is telomere length a biomarker of aging? A review. J. Gerontol. A. Biol. Sci. Med. Sci. 66A(2): 202-213.
Mathers JC (2006) Nutritional modulation of ageing: genomic and epigenetic approaches. Mech Ageing Dev. 127(6): 584-589.
Mecham BH, et al. (2004) Sequence-matched probes produce increased cross-platform consistency and more reproducible biological results in microarray-based gene expression measurements. Nucleic Acids Res. 32(9): e74.
Merrill RM, et al. (2003) Impact of the LDS church's health doctrine on deaths from diseases and conditions associated with cigarette smoking. Ann Epidemiol. 13(10): 704-711.
Monks SA, et al. (2004) Genetic inheritance of gene expression in human cell lines. Am J Hum Genet. 75(6): 1094-1105.
Morley M, et al. (2004) Genetic analysis of genome-wide variation in human gene expression. Nature. 430(7001): 743-747.
Morrison TB, et al. (1998) Quantification of low-copy transcripts by continuous SYBR Green I monitoring during amplification. Biotechniques. 24(6): 954-958, 960, 962.
Mueller P, et al. (2008) Regulation of T cell survival through coronin-1-mediated generation of inositol-1,4,5-trisphosphate and calcium mobilization after T cell receptor triggering. Nat Immunol. 9(4): 424-431.
Nakayama J.I. et al. (Mar. 2002) Stretch PCR Assay. Methods in Molecular Biology. 191: 125-136.
Nebel A, et al. (2005) No association between microsomal triglyceride transfer protein (MTP) haplotype and longevity in humans. Proc Natl Acad Sci USA. 102(22): 7906-7909.
O'Callaghan N, et al. (2008) A quantitative real-time PCR method for absolute telomere length. Biotechniques. 44(6): 807-809.
Powers RW, et al. (2006) Extension of chronological life span in yeast by decreased TOR pathway signaling. Genes Dev. 20(2): 174-184.
Puca AA, et al. (2001) A genome-wide scan for linkage to human exceptional longevity identifies a locus on chromosome 4. Proc Natl Acad Sci USA. 98(18): 10505-10508.
Reiner A, et al. (2003) Identifying differentially expressed genes using false discovery rate controlling procedures. Bioinformatics. 19, 368-375.
Ruchaud S, et al. (2007) Chromosomal passengers: conducting cell division. Nat Rev Mol Cell Biol. 8(10): 798-812.
Rudolph KL, et al. (1999) Longevity, stress response, and cancer in aging telomerase-deficient mice. Cell. 96(5): 701-712.
Rufer N, et al. (1998) Telomere length dynamics in human lymphocyte subpopulations measured by flow cytometry. Nat Biotechnol. 16(8): 743-747.
Rufer, N. et al. (1999) Telomere fluorescence measurements in granulocytes and T lymphocyte subsets point to a high turnover of hematopoietic stem cells and memory T cells in early childhood. J. Exp. Med. 190(2): 157-167.
Ryder MI, et al. (2004) Alteration of gene expression profiles of peripheral mononuclear blood cells by tobacco smoke: implications for periodontal diseases. Oral Microbiol Immunol. 19(1): 39-49.
Schadt EE, et al. (2003) Genetics of gene expression surveyed in maize, mouse and man. Nature. 422(6929): 297-302.
Segal MR (2006) Microarray gene expression data with linked survival phenotypes: diffuse large-B-cell lymphoma revisited. Biostatistics. 7, (2): 268-285.
Seong KH, et al. (2001) Application of the gene search system to screen for longevity genes in *Drosophila*. Biogerontology. 2(3): 209-217.
Sheffield VC, et al. (1989) Attachment of a 40-base-pair G+C-rich sequence (GC-clamp) to genomic DNA fragments by the polymerase chain reaction results in improved detection of single-base changes. Proc Natl Acad Sci USA. 86: 232-236.
Shiow LR, et al. (2008) The actin regulator coronin 1A is mutant in a thymic egress-deficient mouse strain and in a patient with severe combined immunodeficiency. Nat Immunol. 9(11): 1307-1315.
Stranger BE, et al. (2005) Genome-Wide Associations of Gene Expression Variation in Humans. PLoS Genet 1(6): e78.
Svenson U, et al. (2008) Breast cancer survival is associated with telomere length in peripheral blood cells. Cancer Res. 68(10): 3618-3623.
Tatematsu, K. et al. (1996) A novel quantitative 'stretch PCR assay', that detects a dramatic increase in telomerase activity during the progression of myeloid leukemias. Oncogene. 13: 2265-2274.
Therneau TM. (2007) On mixed-effect Cox models, sparse matrices, and modeling data from large pedigrees. Paper presented on Dec. 31, 2007; available at http://mayoresearch.mayo.edu/mayo/research/biostat/upload/kinship.pdf.
Tibshirani R. (1996) Regression Shrinkage and Selection via the Lasso. Journal of the Royal Statistical Society, Series B. 58(1): 267-288.
van Leeuwen DM, et al. (2005) Differential gene expression in human peripheral blood mononuclear cells induced by cigarette smoke and its constituents. Toxicol Sci. 86(1): 200-210.
Wang L, et al. (2007) Cdc42 GTPase-activating protein deficiency promotes genomic instability and premature aging-like phenotypes. Proc Natl Acad Sci USA. 104(4): 1248-1253.
White R, et al. (1985) Construction of linkage maps with DNA markers for human chromosomes. Nature. 313(5998): 101-105.
Wilson CL, et al. (2004) Amplification protocols introduce systematic but reproducible errors into gene expression studies. Biotechniques. 36(3): 498-506.
Wittwer CT, et al. (2001) Real-time multiplex PCR assays. Methods. 25(4): 430-442.
Wu Z, et al. (2005) Stochastic models inspired by hybridization theory for short oligonucleotide arrays. J Comput Biol 12(6): 882-893.
Wylie JE, et al. (2003) Biomedical databases: protecting privacy and promoting research. Trends Biotechnol. 21(3): 113-116.
Yang J, et al. (2007) AZD1152, a novel and selective aurora B kinase inhibitor, induces growth arrest, apoptosis, and sensitization for tubulin depolymerizing agent or topoisomerase II inhibitor in human acute leukemia cells in vitro and in vivo. Blood. 110(6): 2034-2040.
Zhang W, et al. (2007) Gender-specific differences in expression in human lymphoblastoid cell lines. Pharmacogenet Genomics. 17(6): 447-450.
Zhang X, et al. (1999) Telomere shortening and apoptosis in telomerase-inhibited human tumor cells. Genes Dev. 13(18): 2388-2399.
Zijlmans JM, et al. (1997) Telomeres in the mouse have large interchromosomal variations in the Number of T2AG3 repeats. Proc Natl Acad Sci USA. 94(14): 7423-7428.
Office Action issued on Mar. 8, 2011 for Canadian application No. 2513747, which claims priority to PCT/US2004/002215, filed on Jan. 26, 2004. (Applicant—University of Utah; Inventor—Cawthon et al.) (3 pages).
Response to Office Action filed on Sep. 8, 2011 for Canadian application No. 2513747, which claims priority to PCT/US2004/002215, filed on Jan. 26, 2004. (Applicant—University of Utah; Inventor—Cawthon et al.) (23 pages).

(56) References Cited

OTHER PUBLICATIONS

Office Action issued on Apr. 16, 2012 for Canadian application No. 2513747, which claims priority to PCT/US2004/002215, filed on Jan. 26, 2004. (Applicant—University of Utah; Inventor—Cawthon et al.) (3 pages).
Office Action issued on Jan. 22, 2010 for European application No. 04705326.9, which claims priority to PCT/US2004/002215, filed on Jan. 26, 2004. (Applicant—University of Utah; Inventor—Cawthon et al.) (6 pages).
Response to Office Action filed on Jun. 21, 2010 for European application No. 04705326.9, which claims priority to PCT/US2004/002215, filed on Jan. 26, 2004. (Applicant—University of Utah; Inventor—Cawthon et al.) (6 pages).
Office Action issued on Dec. 27, 2011 for European application No. 04705326.9, which claims priority to PCT/US2004/002215, filed on Jan. 26, 2004. (Applicant—University of Utah; Inventor—Cawthon et al.) (7 pages).
Office Action issued Feb. 21, 2012 for European application No. 04705326.9, which claims priority to PCT/US2004/002215, filed on Jan. 26, 2004. (Applicant—University of Utah; Inventor—Cawthon et al.) (2 pages).
Response to Office Action filed Apr. 30, 2012 for European application No. 04705326.9, which claims priority to PCT/US2004/002215, filed on Jan. 26, 2004. (Applicant—University of Utah; Inventor—Cawthon et al.) (1 page).
Supplementary Search Report issued on Jun. 19, 2012 for European application No. 04705326.9, which claims priority to PCT/US2004/002215, filed on Jan. 26, 2004. (Applicant—University of Utah; Inventor—Cawthon et al.) (5 pages).
Response to Office Action filed on Jul. 2, 2012 for European application No. 04705326.9, which claims priority to PCT/US2004/002215, filed on Jan. 26, 2004. (Applicant—University of Utah; Inventor—Cawthon et al.) (2 pages).
Intention to Grant issued Sep. 4, 2012 for European application No. 04705326.9, which claims priority to PCT/US2004/002215, filed on Jan. 26, 2004. (Applicant—University of Utah; Inventor—Cawthon et al. (44 pages).
Office Action issued Feb. 16, 2012 for European application No. 12152681.8, which claims priority to PCT/US2004/002215, filed on Jan. 26, 2004. (Applicant—University of Utah; Inventor—Cawthon et al.) (1 page).
Response to Office Action filed Apr. 26, 2012 for European application No. 12152681.8, which claims priority to PCT/US2004/002215, filed on Jan. 26, 2004. (Applicant—University of Utah; Inventor—Cawthon et al.) (1 page).
Office Action issued on Apr. 27, 2012 for European application No. 12152681.8, which claims priority to PCT/US2004/002215, filed on Jan. 26, 2004. (Applicant—University of Utah; Inventor—Cawthon et al.) (2 pages).
Response to Office Action filed May 14, 2012 for European application No. 12152681.8, which claims priority to PCT/US2004/002215, filed on Jan. 26, 2004. (Applicant—University of Utah; Inventor—Cawthon et al.) (1 page).
Supplementary Search Report issued on Jun. 8, 2012 for European application No. 12152681.8, which claims priority to PCT/US2004/002215, filed on Jan. 26, 2004. (Applicant—University of Utah; Inventor—Cawthon et al.) (11 pages).
Communication pursuant to Rules 70(2) and 70a(2) EPC and reference to Rule 39(1) EPC issued Jul. 16, 2012 for European application No. 12152681.8, which claims priority to PCT/US2004/002215, filed on Jan. 26, 2004. (Applicant—University of Utah; Inventor—Cawthon et al.) (2 pages).
Office Action issued on Nov. 4, 2009 for Japanese application No. 2006-503063, which claims priority to PCT/US2004/002215, filed on Jan. 26, 2004. (Applicant—University of Utah; Inventor—Cawthon et al.) (2 pages).
Response to Office Action issued on Mar. 25, 2010 for Japanese application No. 2006-503063, which claims priority to PCT/US2004/002215, filed on Jan. 26, 2004. (Applicant—University of Utah; Inventor—Cawthon et al.) (4 pages).

Office Action issued on Nov. 16, 2010 for Japanese application No. 2006-503063, which claims priority to PCT/US2004/002215, filed on Jan. 26, 2004. (Applicant—University of Utah; Inventor—Cawthon et al.) (2 pages).
Notice of appeal filed Mar. 16, 2011 for Japanese application No. 2006-503063, which claims priority to PCT/US2004/002215, filed on Jan. 26, 2004. (Applicant—University of Utah; Inventor—Cawthon et al.) (3 pages).
Formality office action issued Apr. 12, 2011 for Japanese application No. 2006-503063, which claims priority to PCT/US2004/002215, filed on Jan. 26, 2004. (Applicant—University of Utah; Inventor—Cawthon et al.) (2 pages).
Appeal brief filed May 24, 2011 for Japanese application No. 2006-503063, which claims priority to PCT/US2004/002215, filed on Jan. 26, 2004. (Applicant—University of Utah; Inventor—Cawthon et al.) (8 pages).
International search report issued Nov. 18, 2004 for PCT/US2004/002215, filed on Jan. 26, 2004. (Applicant—University of Utah; Inventor—Cawthon et al.) (4 pages).
Written opinion of international search report issued Jul. 24, 2005 for PCT/US2004/002215, filed on Jan. 26, 2004. (Applicant—University of Utah; Inventor—Cawthon et al.) (5 pages).
International preliminary report on patentability issued on Jul. 29, 2005 for PCT/US2004/002215, filed on Jan. 26, 2004. (Applicant—University of Utah; Inventor—Cawthon et al.) (6 pages).
National Phase Entry on Aug. 22, 2011 for Chinese application No. 200980157269.8, which claims priority to PCT/US2009/069243, filed on Dec. 22, 2009. (Applicant—University of Utah; Inventor—Cawthon et al.) (1 page).
Notice of Amendment and Completion of Formalities issued on Sep. 29, 2011 for Chinese application No. 200980157269.8, which claims priority to PCT/US2009/069243, filed on Dec. 22, 2009. (Applicant—University of Utah; Inventor—Cawthon et al.) (3 pages).
Response to Notice of Amendment and Completion of Formalities issued on Jan. 19, 2012 for Chinese application No. 200980157269.8, which claims priority to PCT/US2009/069243, filed on Dec. 22, 2009. (Applicant—University of Utah; Inventor—Cawthon et al.) (2 pages).
Notice of Passing Preliminary Exam issued on Feb. 10, 2012 for Chinese application No. 200980157269.8, which claims priority to PCT/US2009/069243, filed on Dec. 22, 2009. (Applicant—University of Utah; Inventor—Cawthon et al.) (1 page).
Amendment before examination filed on Feb. 13, 2012 for European application No. 09804177.5, which claims priority to PCT/US2009/069243, filed on Dec. 22, 2009. (Applicant—University of Utah; Inventor—Cawthon et al.) (18 pages).
Request for Registration and Grant filed on Oct. 22, 2012 for Hong Kong application No. 12110505.3, which claims priority to PCT/US2009/069243, filed on Dec. 22, 2009. (Applicant—University of Utah; Inventor—Cawthon et al.) (1 page).
International search report issued Mar. 30, 2010 for PCT/US2009/069243, filed on Dec. 22, 2009. (Applicant—University of Utah; Inventor—Cawthon et al.) (5 pages).
Written opinion of international search report issued Jun. 22, 2011 for PCT/US2009/069243, filed on Dec. 22, 2009. (Applicant—University of Utah; Inventor—Cawthon et al.) (5 pages).
International preliminary report on patentability issued on Jun. 22, 2011 for PCT/US2009/069243, filed on Dec. 22, 2009. (Applicant—University of Utah; Inventor—Cawthon et al.) (6 pages).
Preliminary Amendment filed on Jun. 22, 2011 for U.S. Appl. No. 13/141,429, which claims priority to PCT/US2009/069243, filed Dec. 22, 2009. (Applicant—University of Utah; Inventor—Cawthon et al.) (3 pages).
Request for examination filed on May 3, 2006 for Australian application No. 2003208902, which claims priority to PCT/US2003/002844, filed on Jan. 31, 2003. (Applicant—University of Utah; Inventor—Cawthon et al.) (1 page).
Office Action issued on Mar. 29, 2007 for Australian application No. 2003208902, which claims priority to PCT/US2003/002844, filed on Jan. 31, 2003. (Applicant—University of Utah; Inventor—Cawthon et al.) (2 pages).

(56) References Cited

OTHER PUBLICATIONS

Response to Office Action filed on Jul. 23, 2008 for Australian application No. 2003208902, which claims priority to PCT/US2003/002844, filed on Jan. 31, 2003. (Applicant—University of Utah; Inventor—Cawthon et al.) (16 pages).
Notice of Acceptance issued on Jul. 25, 2008 for Australian application No. 2003208902, which claims priority to PCT/US2003/002844, filed on Jan. 31, 2003. (Applicant—University of Utah; Inventor—Cawthon et al.) (7 pages).
Preliminary Amendment filed on Sep. 20, 2004 for Canadian application No. 2474468, which claims priority to PCT/US2003/002844, filed on Jan. 31, 2003. (Applicant—University of Utah; Inventor—Cawthon et al.) (3 pages).
Office Action issued on Jul. 22, 2010 for Canadian application No. 2474468, which claims priority to PCT/US2003/002844, filed on Jan. 31, 2003. (Applicant—University of Utah; Inventor—Cawthon et al.) (4 pages).
Response to Office Action filed on Jan. 20, 2011 for Canadian application No. 2474468, which claims priority to PCT/US2003/002844, filed on Jan. 31, 2003. (Applicant—University of Utah; Inventor—Cawthon et al.) (3 pages).
Office Action issued on Jul. 13, 2011 for Canadian application No. 2474468, which claims priority to PCT/US2003/002844, filed on Jan. 31, 2003. (Applicant—University of Utah; Inventor—Cawthon et al.) (2 pages).
Response to Office Action filed on Jan. 13, 2012 for Canadian application No. 2474468, which claims priority to PCT/US2003/002844, filed on Jan. 31, 2003. (Applicant—University of Utah; Inventor—Cawthon et al.) (3 pages).
Office Action issued on May 29, 2012 for Canadian application No. 2474468, which claims priority to PCT/US2003/002844, filed on Jan. 31, 2003. (Applicant—University of Utah; Inventor—Cawthon et al.) (2 pages).
Office Action issued on Mar. 17, 2006 for Chinese application No. 03804867.1, which claims priority to PCT/US2003/002844, filed on Jan. 31, 2003. (Applicant—University of Utah; Inventor—Cawthon et al.) (4 pages).
Response to Office Action filed on Sep. 19, 2006 for Chinese application No. 03804867.1, which claims priority to PCT/US2003/002844, filed on Jan. 31, 2003. (Applicant—University of Utah; Inventor—Cawthon et al.) (4 pages).
Notice of Acceptance issued on Apr. 1, 2009 for Chinese application No. 03804867.1, which claims priority to PCT/US2003/002844, filed on Jan. 31, 2003. (Applicant—University of Utah; Inventor—Cawthon et al.) (2 pages).
Request for examination filed on Aug. 20, 2004 for European application No. 03707624.7, which claims priority to PCT/US2003/002844, filed on Jan. 31, 2003. (Applicant—University of Utah; Inventor—Cawthon et al.) (7 pages).
Office Action issued on Oct. 26, 2006 for European application No. 03707624.7, which claims priority to PCT/US2003/002844, filed on Jan. 31, 2003. (Applicant—University of Utah; Inventor—Cawthon et al.) (7 pages).
Response to Office Action filed on Aug. 21, 2007 for European application No. 03707624.7, which claims priority to PCT/US2003/002844, filed on Jan. 31, 2003. (Applicant—University of Utah; Inventor—Cawthon et al.) (9 pages).
Office Action issued on Dec. 13, 2007 for European application No. 03707624.7, which claims priority to PCT/US2003/002844, filed on Jan. 31, 2003. (Applicant—University of Utah; Inventor—Cawthon et al.) (6 pages).
Response to Office Action filed on Sep. 17, 2008 for European application No. 03707624.7, which claims priority to PCT/US2003/002844, filed on Jan. 31, 2003. (Applicant—University of Utah; Inventor—Cawthon et al.) (7 pages).
Office Action issued on Oct. 13, 2010 for European application No. 03707624.7, which claims priority to PCT/US2003/002844, filed on Jan. 31, 2003. (Applicant—University of Utah; Inventor—Cawthon et al.) (6 pages).
Response to Office Action filed on Jan. 18, 2011 for European application No. 03707624.7, which claims priority to PCT/US2003/002844, filed on Jan. 31, 2003. (Applicant—University of Utah; Inventor—Cawthon et al.) (20 pages).
Intention to Grant issued Jun. 6, 2011 for European application No. 03707624.7, which claims priority to PCT/US2003/002844, filed on Jan. 31, 2003. (Applicant—University of Utah; Inventor—Cawthon et al.) (5 pages).
Request for Registration filed on Feb. 11, 2012 for Hong Kong application No. 05103554.7, which claims priority to PCT/US2003/002844, filed on Jan. 31, 2003. (Applicant—University of Utah; Inventor—Cawthon et al.) (1 page).
Certificate of Grant issued Jun. 15, 2012 for Hong Kong application No. 05103554.7, which claims priority to PCT/US2003/002844, filed on Jan. 31, 2003. (Applicant—University of Utah; Inventor—Cawthon et al.) (4 pages).
Request for examination and Preliminary Amendment filed on Jan. 31, 2006 for Japanese application No. 2003-564211, which claims priority to PCT/US2003/002844, filed on Jan. 31, 2003. (Applicant—University of Utah; Inventor—Cawthon et al.) (1 page).
Office Action issued on Oct. 7, 2008 for Japanese application No. 2003-564211, which claims priority to PCT/US2003/002844, filed on Jan. 31, 2003. (Applicant—University of Utah; Inventor—Cawthon et al.) (2 pages).
Response to Office Action filed on Apr. 7, 2009 for Japanese application No. 2003-564211, which claims priority to PCT/US2003/002844, filed on Jan. 31, 2003. (Applicant—University of Utah; Inventor—Cawthon et al.) (4 pages).
Office Action issued on May 7, 2009 for Japanese application No. 2003-564211, which claims priority to PCT/US2003/002844, filed on Jan. 31, 2003. (Applicant—University of Utah; Inventor—Cawthon et al.) (1 page).
Response to Office Action filed on Sep. 7, 2009 for Japanese application No. 2003-564211, which claims priority to PCT/US2003/002844, filed on Jan. 31, 2003. (Applicant—University of Utah; Inventor—Cawthon et al.) (6 pages).
Office Action issued on Nov. 4, 2009 for Japanese application No. 2003-564211, which claims priority to PCT/US2003/002844, filed on Jan. 31, 2003. (Applicant—University of Utah; Inventor—Cawthon et al.) (1 page).
Response to Office Action filed on Apr. 27, 2010 for Japanese application No. 2003-564211, which claims priority to PCT/US2003/002844, filed on Jan. 31, 2003. (Applicant—University of Utah; Inventor—Cawthon et al.) (1 page).
Notice of Grant and Translated Claims issued May 21, 2010 for Japanese application No. 2003-564211, which claims priority to PCT/US2003/002844, filed on Jan. 31, 2003. (Applicant—University of Utah; Inventor—Cawthon et al.) (21 pages).
International search report issued Feb. 26, 2004 for PCT/US2003/002844, filed on Jan. 31, 2003. (Applicant—University of Utah; Inventor—Cawthon et al.) (3 pages).
International preliminary report on patentability issued on Nov. 16, 2004 for PCT/US2003/002844, filed on Jan. 31, 2003. (3 pages).
Preliminary Amendment filed on Apr. 29, 2003 for U.S. Appl. No. 10/355,626, which claims priority to PCT/US2003/002844, filed Jan. 31, 2003. (Applicant—University of Utah; Inventor—Cawthon et al.) (9 pages).
Preliminary Amendment filed on Feb. 17, 2005 for U.S. Appl. No. 10/355,626, which claims priority to PCT/US2003/002844, filed Jan. 31, 2003. (Applicant—University of Utah; Inventor—Cawthon et al.) (9 pages).
Restriction Requirement issued on May 2, 2006 for U.S. Appl. No. 10/355,626, which claims priority to PCT/US2003/002844, filed Jan. 31, 2003. (Applicant—University of Utah; Inventor—Cawthon et al.) (18 pages).
Response to Restriction Requirement filed on Mar. 2, 2007 for U.S. Appl. No. 10/355,626, which claims priority to PCT/US2003/002844, filed Jan. 31, 2003. (Applicant—University of Utah; Inventor—Cawthon et al.) (19 pages).
Office Action issued on Aug. 6, 2007 for U.S. Appl. No. 10/355,626, which claims priority to PCT/US2003/002844, filed Jan. 31, 2003. (Applicant—University of Utah; Inventor—Cawthon et al.) (18 pages).

(56) References Cited

OTHER PUBLICATIONS

Response to Office Action filed on Jan. 22, 2008 for U.S. Appl. No. 10/355,626, which claims priority to PCT/US2003/002844, filed Jan. 31, 2003. (Applicant—University of Utah; Inventor—Cawthon et al.) (19 pages).
Office Action issued on Mar. 27, 2008 for U.S. Appl. No. 10/355,626, which claims priority to PCT/US2003/002844, filed Jan. 31, 2003. (Applicant—University of Utah; Inventor—Cawthon et al.) (18 pages).
Response to Office Action filed on Jun. 27, 2008 for U.S. Appl. No. 10/355,626, which claims priority to PCT/US2003/002844, filed Jan. 31, 2003. (Applicant—University of Utah; Inventor—Cawthon et al.) (10 pages).
Notice of Appeal filed on Sep. 26, 2008 for U.S. Appl. No. 10/355,626, which claims priority to PCT/US2003/002844, filed Jan. 31, 2003. (Applicant—University of Utah; Inventor—Cawthon et al.) (1 page).
Advisory Action issued on Oct. 7, 2008 for U.S. Appl. No. 10/355,626, which claims priority to PCT/US2003/002844, filed Jan. 31, 2003. (Applicant—University of Utah; Inventor—Cawthon et al.) (3 pages).
Office Action issued on Jan. 22, 2009 for U.S. Appl. No. 10/355,626, which claims priority to PCT/US2003/002844, filed Jan. 31, 2003. (Applicant—University of Utah; Inventor—Cawthon et al.) (8 pages).
Response to Office Action filed on Jul. 22, 2009 for U.S. Appl. No. 10/355,626, which claims priority to PCT/US2003/002844, filed Jan. 31, 2003. (Applicant—University of Utah; Inventor—Cawthon et al.) (11 pages).
Notice of Allowance issued on Nov. 17, 2009 for U.S. Appl. No. 10/355,626, which claims priority to PCT/US2003/002844, filed Jan. 31, 2003. (Applicant—University of Utah; Inventor—Cawthon et al.) (6 pages).
Restriction Requirement issued on Jul. 8, 2010 for U.S. Appl. No. 12/700,475, which claims priority to PCT/US2003/002844, filed Jan. 31, 2003. (Applicant—University of Utah; Inventor—Cawthon et al.) (6 pages).
Response to Restriction Requirement filed on Aug. 9, 2010 for U.S. Appl. No. 12/700,475, which claims priority to PCT/US2003/002844, filed Jan. 31, 2003. (Applicant—University of Utah; Inventor—Cawthon et al.) (10 pages).
Office Action issued on Oct. 28, 2010 for U.S. Appl. No. 12/700,475, which claims priority to PCT/US2003/002844, filed Jan. 31, 2003. (Applicant—University of Utah; Inventor—Cawthon et al.) (8 pages).
Response to Office Action filed on Mar. 28, 2011 for U.S. Appl. No. 12/700,475, which claims priority to PCT/US2003/002844, filed Jan. 31, 2003. (Applicant—University of Utah; Inventor—Cawthon et al.) (14 pages).
Supplemental Application Data Sheet filed on Jun. 15, 2011 for U.S. Appl. No. 12/700,475, which claims priority to PCT/US2003/002844, filed Jan. 31, 2003. (Applicant—University of Utah; Inventor—Cawthon et al.) (14 pages).
Notice of Allowance issued on Jun. 27, 2011 for U.S. Appl. No. 12/700,475, which claims priority to PCT/US2003/002844, filed Jan. 31, 2003. (Applicant—University of Utah; Inventor—Cawthon et al.) (10 pages).
Issue Notification mailed Mar. 24, 2010 by the USPTO for U.S. Appl. No. 10/355,626, filed Jan. 21, 2003 [Inventor—Cawthon; Applicant—University of Utah Research Foundation] [1 page].
Issue Notification mailed Oct. 12, 2011 by the USPTO for U.S. Appl. No. 12/700,475, filed Feb. 4, 2010 [Inventor—Cawthon; Applicant—University of Utah Research Foundation] [1 page].
Non-Final Office Action issued on Jan. 23, 2015 by the USPTO for U.S. Appl. No. 13/141,429, filed Aug. 15, 2011 (Inventor—Cawthorn; Applicant University of Utah Research Foundation) (8 pages).

* cited by examiner

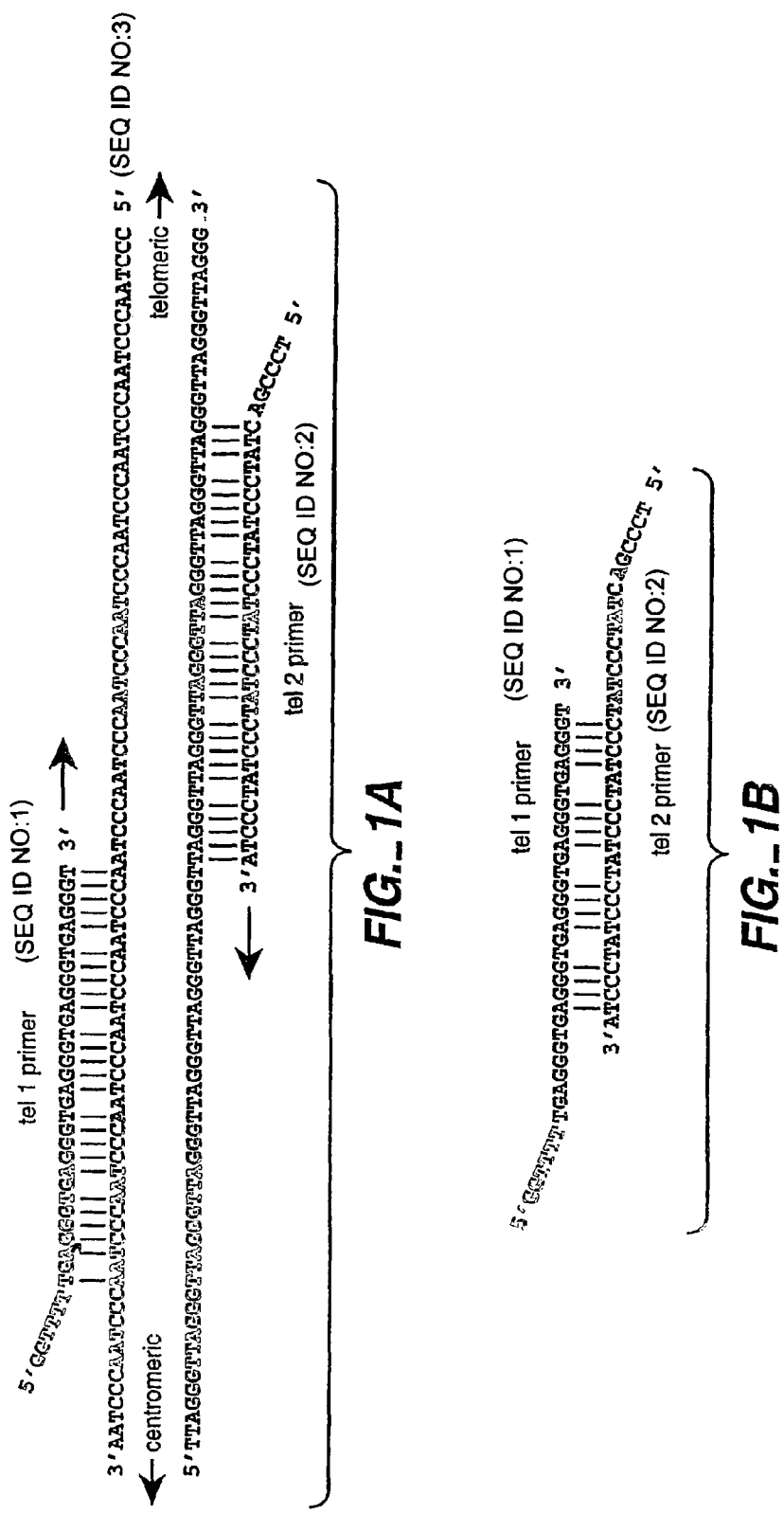

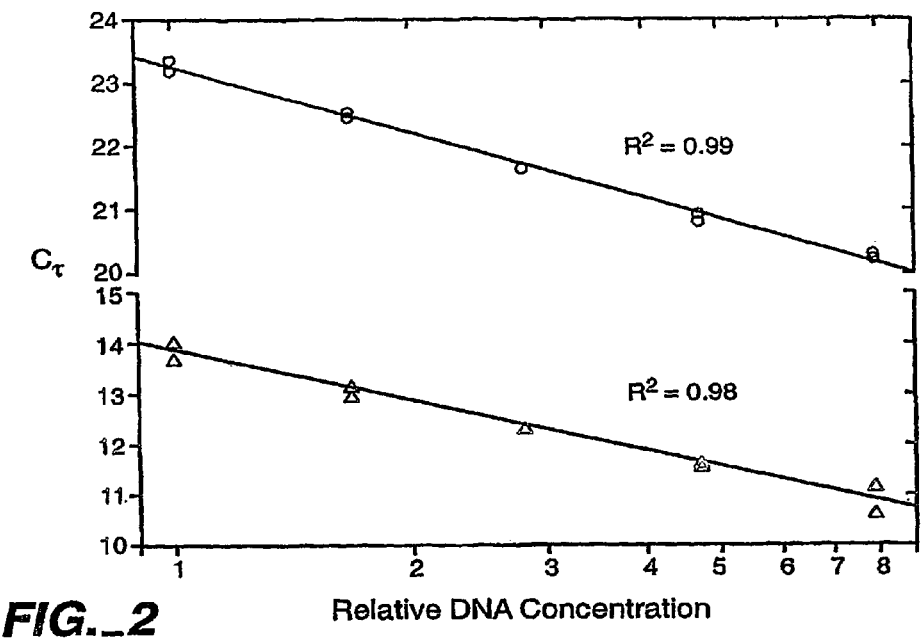
FIG._2
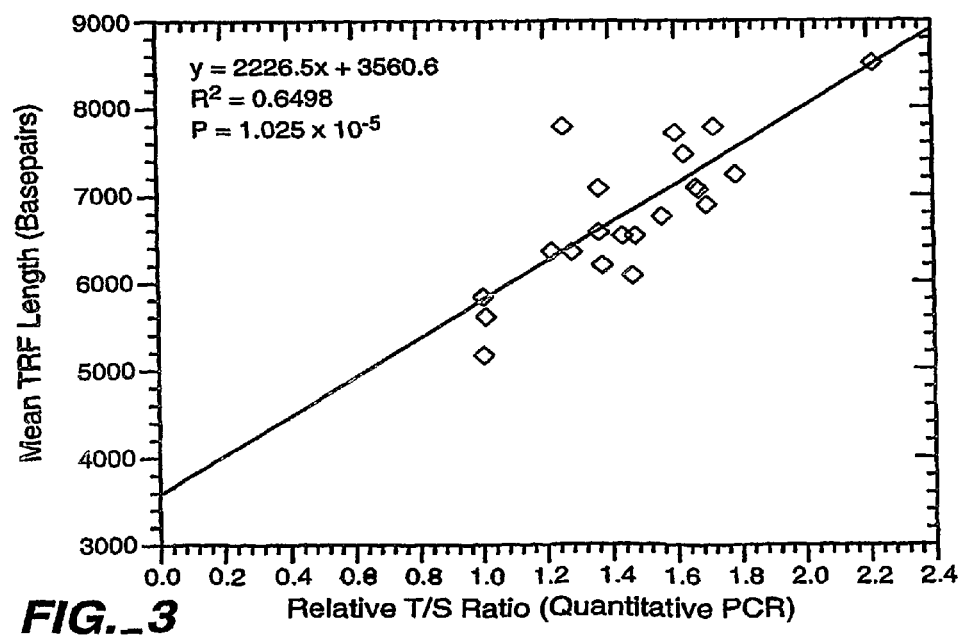
FIG._3

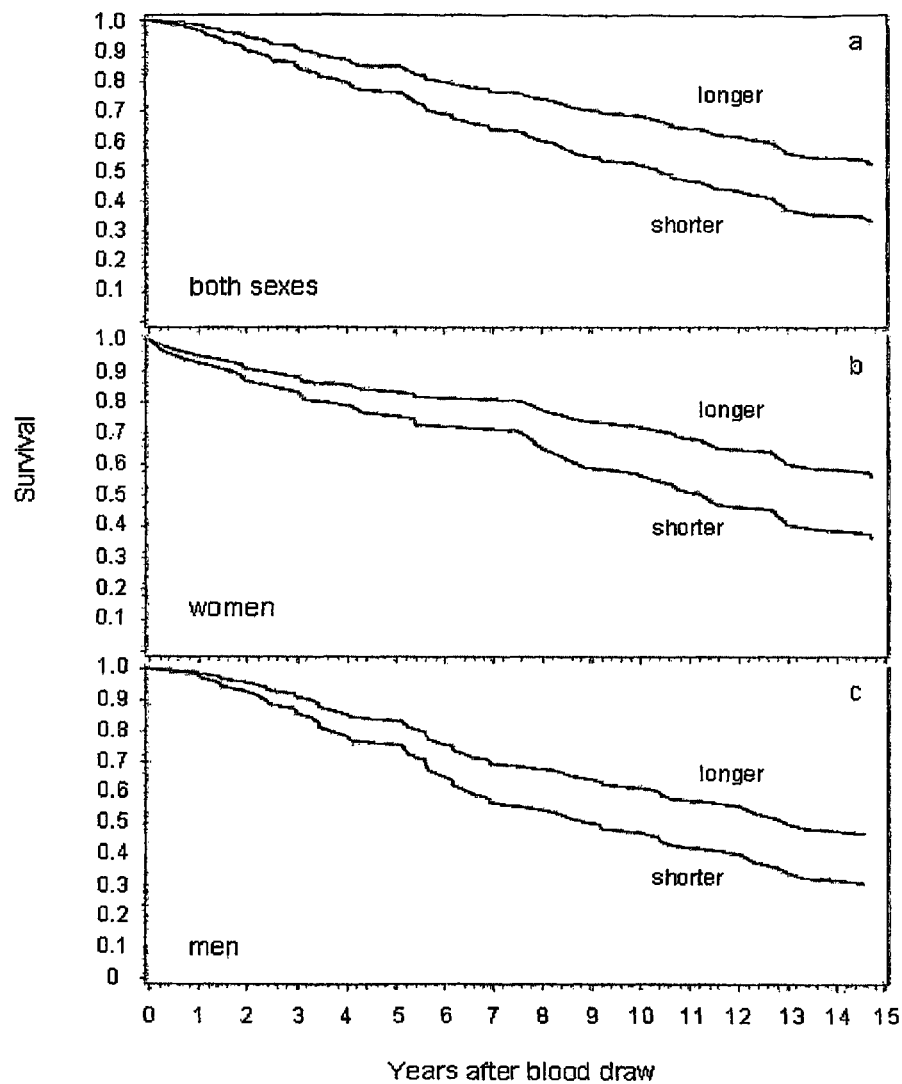
FIG._4

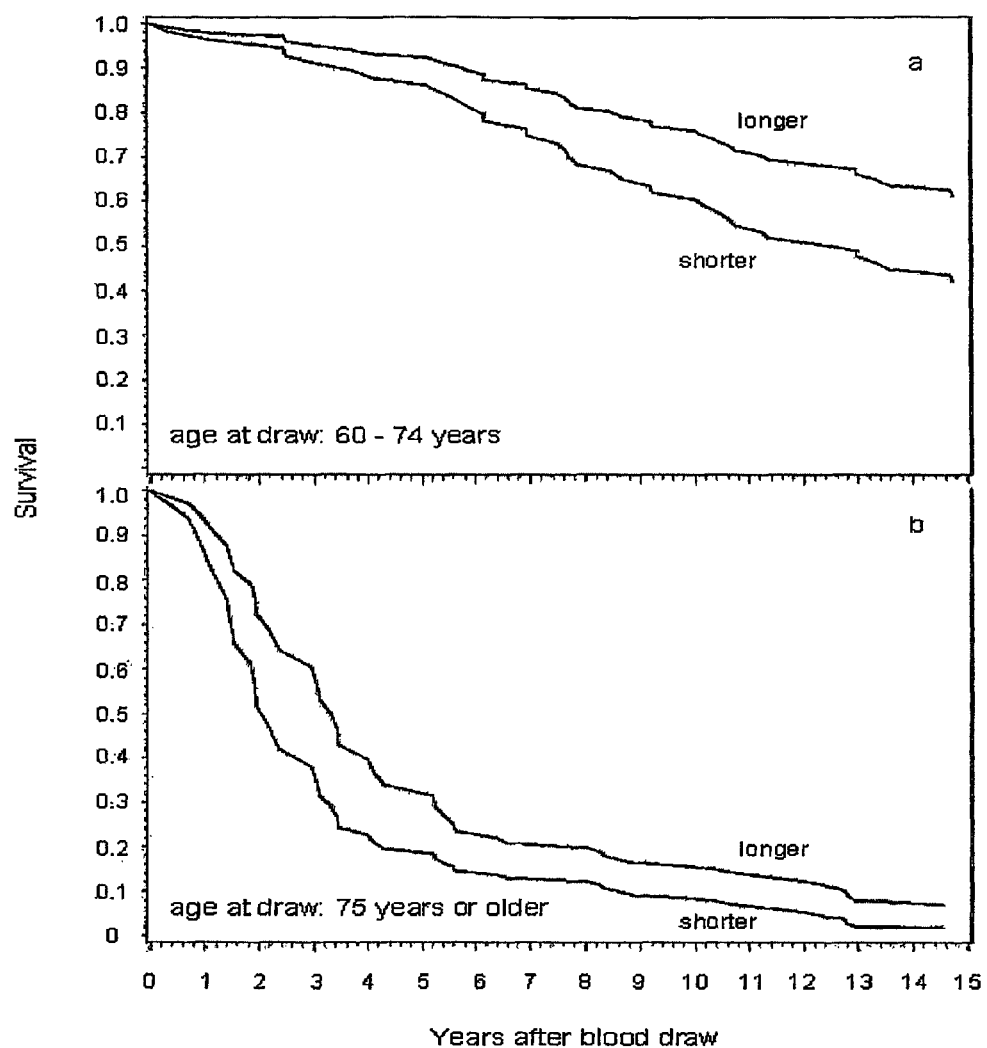
FIG._5

METHODS OF PREDICTING MORTALITY RISK BY DETERMINING TELOMERE LENGTH

CROSS REFERENCES TO RELATED APPLICATIONS

This application claims the benefit of U.S. Provisional Application No. 60/442,456, filed Jan. 24, 2003, the entire contents of which is incorporated herein by reference.

TECHNICAL FIELD

The present invention relates to methods of predicting mortality rates, and in particular to methods for determining the length of telomeres and correlating telomere length with survival, mortality risk, and suceptibility to age related diseases, such as cardiovascular disease, neoplastic disease, and infectious disease. The invention further relates to use of the methods to identify individuals or groups of individuals at risk of developing such age related diseases.

BACKGROUND OF THE INVENTION

Telomeres are specialized structures present at the ends of linear eukaryotic chromosomes that function in replicating and maintaining the integrity of the chromosomal ends. Telomeres distinguish the chromosomal terminus from other types of double stranded breaks responsible for initiating cell growth arrest and aberrant chromosomal fusions.

Telomeric sequences vary between species, but their essential features are similar between eukaryotes. The telomeric DNA is generally composed of tandem repeats of a basic sequence unit. Telomeric repeats of some organisms are perfect repeats, such as sequence TTAGGG seen in humans or slime mold. Others, such as those of yeast or protozoans, have irregular repeat sequences. In general, the G rich strand runs 5' to 3' to the chromosomal terminus. The length of the repeat sequences range from a few to tens of kilo base pairs.

In some organisms, the characteristic telomeric repeat sequences are absent and are substituted by other sequences that function similar to telomere repeat sequences. For example, in *Drosophila melanogaster*, the telomeres are generally composed of non-LTR—type retrotransposons, called HeT-A and TART elements. In the mosquito *Anopheles gambiae*, the chromosomal ends are composed of arrays of complex sequence tandem repeats rather than short repeat sequences.

In some organisms, a 3' single stranded overhang is present at the terminus of the telomere. The length of the single stranded region is variable, extending from about 100 bp or more. Under defined conditions in vivo or in vitro, the overhanging terminus associates with various telomere associated proteins and invades the double stranded telomere region to form t-loop structures (Griffith, J. D. et al., *Cell* 97: 503-514 (1999); Munoz-Jordan et al., *EMBO J.* 20: 579-588 (2001)). Formation oft-loop structures is believed to function in negatively regulating telomere elongation by telomerase, and in addition, provide a mechanism for sequestering the single stranded ends to protect them from degradation and to suppress activation of DNA damage checkpoint pathways.

Typically, the DNA replicative machinery acts in the 5' to 3' direction, and synthesis of the lagging strand occurs discontinuously by use of short RNA primers that are degraded following strand synthesis. Since sequences at the 3' end of a linear DNA are not available to complete synthesis of the region previously occupied by the RNA primer, the terminal 3' region of the linear chromosome is not replicated. This "end replication problem" is solved by the action of telomerase, a telomere specific ribonucleoprotein reverse transcriptase. The telomerase enzyme has an integral RNA component that acts as a template for extending the 3' end of the telomere. Repeated extensions by telomerase activity results in the generation of telomere repeats copied from the telomerase-bound RNA template. Following elongation by telomerase, lagging strand synthesis by DNA polymerase completes formation of the double stranded telomeric structure.

In normal human somatic cells, telomerase is not expressed or expressed at low levels. Consequently, telomeres shorten by 50-200 bp with each cell division until the cells reach replicative senescence, at which point the cells loose the capacity to proliferate. This limited capacity of cells to replicate is generally referred to as the Hayflick limit, and may provide cells with a counting mechanism, i.e., a mitotic clock, to count cell divisions and regulate cellular development. Correspondingly, activation of telomerase in cells lacking telomerase activity, for example by expressing telomerase from a constitute retroviral promoter or activation of endogenous polymerase, allows the cells to maintain proliferative capacity and leads to immortalization of the cell.

Interestingly, these immortalized cells have short stable telomeres while the shortest telomeres become extended. This phenomena suggests that telomerase enzyme protects short telomeres from further shortening while extending those that have fallen below a certain threshold length. Thus, presence of telomerase activity does not appear to be necessary when telomeres are a certain length, but becomes critical to maintenance of telomere integrity when it falls below a critical limit.

It is well established that the length and integrity of telomeres is important for proper segregation of chromosomes and cell growth. For example, development of many types of cancers correlates with activation of telomere maintenance while cell senescence correlates with loss of telomere integrity. Shortening of telomere induced by inhibiting telomerase activity can lead to proliferative senescence and cell apoptosis (Zhang, X. et al., *Genes Dev.* 2388-99 (1999)). Moreover, genetic knockouts of telomerase RNA in mice results in animals with developmental defects, age related pathologies, and increased cancer susceptibility (Rudolph, K. L. et al., *Cell* 96: 701-12 (1999); Herrera, E. et al., *EMBO J.* 18: 2950-60 (1999)). Similarly, in the autosomal dominant disorder of dyskeratosis congenita (DKC), which arises from a mutation in the gene encoding the RNA component of telomerase, afflicted patients display accelerated telomere shortening and die at a median age of 16 years (maximum approximately 50 years), usually from severe infections secondary to bone marrow failure. Clinical features of DKC patients, further suggestive of accelerated aging, include premature graying and loss of hair; skin dyspigmentation; poor wound healing; high risk of severe infections; and an increased incidence of malignancies, osteoporosis, and pulmonary fibrosis. In addition, the shortest average telomere lengths measured in blood DNA from normal elderly individuals overlap with the highest average telomere lengths measured in blood from DKC patients.

In view of the role telomeres play in cell growth and cell senescence, it is desirable to have methods of predicting the occurrence of age related diseases and mortality risk based on length of telomeres. This will provide a basis for identifying individuals with increased risk of developing particular age-associated diseases, such as cancer and hypertension, such that early medical intervention can be administered to individuals in high risk groups. In addition, these methods can be used to identify genetic and environmental factors that may play a role in changing the aging process or altering disease susceptibility in individuals and in populations.

SUMMARY OF THE INVENTION

In accordance with the above objects of the invention, the present invention provides methods of determining telomere length and associating the measured telomere length with a Mortality risk or likelihood of disease occurrence that corresponds to a telomere length observed in a population.

Various methods for measuring telomere length are provided, including measuring mean terminal restriction fragment (TRF), quantitative fluorescent in situ hybridization, flow cytometry, and polymerase chain reaction. In a preferred embodiment, the telomere length is measured using PCR and telomere specific primers designed to amplify telomere repeat sequences. This provides a rapid method to measure average telomere length within a cell or population of cells and is particularly suited for large-scale population studies.

In one embodiment, the telomere length is measured from somatic cells, particularly those that show low or no levels telomerase activity. Suitable samples are derived from blood, and particularly the lymphoid cells in the blood.

The telomere length is determined for an individual and correlated with telomere length observed in a population. The mortality rate within the population is assessed relative to telomere length. In a preferred embodiment, the population is aged matched with the age of the individual organism being examined. For humans, the age-matched population is within about 10 years of the age of the individual, more preferable within 5 years, and most preferable within one year.

Correlation of the measured telomere length of the individual and the population is examined by various statistical methods, such as survival analysis, including Cox proportional hazard regression models, Kaplan-Meier survival distribution estimate, Peto Wilcoxon test, maximum likelihood analysis, multiple regression analysis, and others.

In another embodiment, the mortality risk is determined for rate of telomere shortening and mortality within a population. The rate at which the telomere shortens for an individual is measured to determine the mortality risk to that individual.

In another embodiment, the methods of the present invention is used to predict the likelihood of occurrence of age related diseases in a population and individuals within the population. Age related diseases that may be examined, include, but are not limited to, cardiovascular disease (e.g., hypertension, myocardial infarction, stroke, etc.), neoplastic diseases (e.g., cancers, carcinomas, malignant tumors, etc.), and susceptibility to infectious diseases.

BRIEF DESCRIPTION OF THE DRAWINGS

FIG. 1 depicts the sequence of the oligonucleotide primer pairs, tel-1 (SEQ ID NO:1) and tel-2 (SEQ ID NO:2), used to amplify human telomeric repetitive units. Shown are the hybridization schemes of the primers to the telomere repetitive sequences (SEQ ID NO: 3 and 4) and hybridization of the primers to each other. The tel-1 primer can hybridize to any available complementary 31 basepair stretch along the strand of telomeric DNA oriented 5' to 3' toward the centromere. The tel-2 primer can hybridize to any complementary 33 basepair stretch along the strand oriented 5' to 3' toward the end of the chromosome. For each primer, nucleotide residues are altered to produce mismatches between the altered residue and nucleotide residues at the identical nucleotide position of each repetitive unit to which the primer hybridizes. Thus, for tel-1 and tel-2, every sixth base is mismatched. To limit primer-dimer products, the altered residues of each primer also produces a mismatch with the 3' terminal nucleotide residue of the other primer when the primers hybridize to each other, thus blocking extension by polymerase. In addition, the 5' terminal regions of the primer are designed so as to not basepair with the telomeric repeats. These noncomplementary 5' terminal sequences prevent the 3' ends of the PCR products from initiating DNA synthesis in the middle of telomere amplification products.

FIG. 2 shows standard curves used to measure relative T/S ratios, where the T/S ratio is the telomere (T) to single copy gene (S) ratio (see Example 2). Five DNA concentrations over an eight-fold range were generated by serial dilution (dilution factor ~1.68) and aliquoted into microtiter plate wells; the final amounts per well ranged from 12.64 ng to 100 ng, with the middle quantity approximately matching that of the samples being assayed. The $C_t$ of a DNA sample is the fractional number of PCR cycles to which the sample must be subjected in order to accumulate enough products to cross a set threshold of magnitude of fluorescent signal. Any individual or pooled human DNA sample may be used to create the standard curves, as long as each assayed sample's $C_t$ falls within the range of $C_t$'s of the standard curves. O=single copy gene 36B4; Δ=telomere.

FIG. 3 shows the correlation of relative T/S ratios determined by real time quantitative PCR using the primers described herein and the mean telomere restriction fragment (TRF) lengths determined by traditional Southern hybridization analysis. The DNA samples used for the analysis were from blood drawn from 21 individuals. All relative T/S ratios plotted have values ≥1.0 because the initial T/S ratios determined using the standard curves have all been normalized to the lowest T/S ratio (0.69) observed among the samples. The equation for the linear regression line best fitting the data is shown.

FIG. 4 shows association of telomere length (TL) in blood DNA after age 60 with subsequent survival. The graph shows the proportion of the original sample of research subjects who remained alive (y axis) at various time points (x axis) after the blood draw. In each panel "longer" identifies individuals from the top half of the TL distribution, and "shorter" identifies individuals from the bottom half of the distribution: a, both sexes combined; b, women.; c, men. Data are plotted as fitted survival curves, according to the group prognosis method (Ghali, W. A. et al., JAMA 286: 1494-1497 (2001), incorporated herein by reference).

FIG. 5 shows association of telomere length (TL) in subjects aged 60-74 years, and in subjects aged 75 years or older, with subsequent survival. The graph shows the proportion of the original sample of research subjects who remained alive (y axis) at various time points (x axis) after the blood draw: a, subjects who were age 60-74 years at the time of the blood draw; b, subjects who were age 75 years or older at blood draw. In each panel "longer" identifies individuals from the top half of the TL distribution, and "shorter" identifies individuals from the bottom half of the distribution.

DETAILED DESCRIPTION OF THE INVENTION

The present invention provides methods for predicting the survival or the mortality risk of a eukaryotic organism. Specifically, the method relates to determining the length of telomeres and correlating the telomere length with mortality risk associated with telomere length in a population. The present invention further provides methods of determining telomere length and correlating the length with occurrence of diseases associated with age, such a cardiovascular disease (e.g., hypertension, myocardial infarction, etc.), neoplastic diseases (e.g., malignant tumors, sarcomas, etc.), neurodegenerative disorders, and increased susceptibility to infectious agents. In a further aspect, the present invention provides methods to determine the biological age, as opposed to chronological age, to provide a marker for correlating the biological age with disease susceptibility and mortality risk.

The method of the present invention is useful in a variety of applications. Mortality or survival estimates based on telomere length gives a basis for identifying individuals or groups of individuals for therapeutic intervention or medical screening. It is also useful in epidemiological studies for identifying environmental agents, for example dietary factors, pathological agents, chemical toxins associated with telomere length and mortality. Similarly, the method may be used to identify genetic factors, genetic linkage markers, or genes affecting telomere length and age related diseases.

As discussed above, telomeres are specialized structures found at the ends of linear chromosomes of eukaryotes. Telomeres are generally composed of short tandem repeats, with a repeat sequence unit specified by the telomerase enzyme particular to that organism. Telomere repeat sequences are known for a variety of organisms. For vertebrates, plants, certain types of molds, and some protozoans, the sequences are a perfect repeats. For example, the human repeat sequence unit is $(TTAGGG)_n$.(SEQ ID NO:5) In other organisms, the repeats sequences are irregular, such as those of *Sacharomyces cerevisiae* where the sequence is variable G1-3T/C1-3A. In some eukaryotic organisms, telomeres lack the short tandem sequence repeats but have sequence elements that function as telomeres. For example, in the fruit fly *Drosophila melanogaster*, the telomere is a composite of retrotransposon elements HeT-A and TART while in the mosquito *Anopheles gambiae* the telomeres are arrays of complex sequence tandem repeats. For the purposes of the present invention, telomeres of different structures are encompassed within the scope of the present invention.

In addition to the repeat sequences, the 3' end of some telomeres contains a single stranded region, which for humans is located on the G rich strand. The single strand is composed of $(TTAGGG)_n$ (SEQ ID NO:5) repeats, with n being generally about 9-35, although it can be less or more. As used herein, the length of the 3' single stranded region can also be correlated with mortality risk.

In one embodiment, telomere length may be determined for a single chromosome in a cell. In another embodiment, the average telomere length or mean telomere length is measured for a single cell, and more preferably for a population of cells. A change in telomere length is an increase or decrease in telomere length, in particular an increase or decrease in the average telomere length. The change may be relative to a particular time point, i.e., telomere length of an organism at time $t_1$ as compared to telomere length at some later time $t_2$. A change or difference in telomere length may also be compared as against the average or mean telomere length of a particular cell population or organismal population, preferably those members of a population not suffering from a disease condition. In certain embodiments, change in telomere length is measured against a population existing at different time periods.

Although, telomere lengths may be determined for all eukaryotes, in a preferred embodiment, telomere lengths are determined for vertebrates, including without limitation, amphibians, birds, and mammals, for example rodents, ungulates, and primates, particularly humans. Preferred are organisms in which longevity is a desirable trait or where longevity and susceptibility to disease are correlated. In another aspect, the telomeres may be measured for cloned organisms in order to assess the mortality risk or disease susceptibility associated with altered telomere integrity in these organisms.

Samples for measuring telomeres are made using methods well known in the art. The telomere containing samples may be obtained from any tissue of any organism, including tissues of blood, brain, bone marrow, lymph, liver spleen, breast, and other tissues, including those obtained from biopsy samples. Tissue and cells may be frozen or intact. The samples may also comprise bodily fluids, such as saliva, urine, feces, cerebrospinal fluid, semen, etc. Preferably, the tissue or cells are non-stem cells, i.e., somatic cells since the telomeres of stem cells generally do not decrease over time due to continued expression of telomerase activity. However, in some embodiments, telomeres may be measured for stems cells in order to assess inherited telomere characteristics of an organism.

As used herein telomeric nucleic acids and other "target nucleic acids" or "target sequence" is meant a nucleic acid sequence on a double or single stranded nucleic acid. By "nucleic acid" or "oligonucleotide" or grammatical equivalents herein is meant at least two nucleotides covalently linked together. A nucleic acid of the present invention will generally contain phosphodiester bonds, although in some cases, nucleic acid analogs are included that may have alternate backbones, comprising, for example, phosphoramide (Beaucage, S. L. et al., *Tetrahedron* 49: 1925-63 (1993), and references therein; Letsinger, R. L. et al., *J. Org. Chem.* 35: 3800-03 (1970); Sprinzl, M. et al., *Eur. J. Biochem.* 81: 579-89 (1977); Letsinger, R. L. et al., *Nucleic Acids Res.* 14:3487-99 (1986); Sawai et al, *Chem. Lett.* 805 (1984); Letsinger, R. L. et al., *J. Am. Chem. Soc.* 110: 4470 (1988); and Pauwels et al., *Chemica Scripta* 26:141-49 (1986)), phosphorothioate (Mag, M. et al., *Nucleic Acids Res.* 19:1437-41 (1991); and U.S. Pat. No. 5,644,048), phosphorodithioate (Briu et al., *J. Am. Chem. Soc.* 111:2321 (1989)), O-methylphophoroamidite linkages (see Eckstein, *Oligonucleotides and Analogues: A Practical Approach*, Oxford University Press, 1991), and peptide nucleic acid backbones and linkages (Egholm, M., *Am. Chem. Soc.* 114:1895-97 (1992); Meier et al., *Chem. Int. Ed. Engl.* 31:1008 (1992); Egholm, M., *Nature* 365: 566-68 (1993); Carlsson, C. et al., *Nature* 380: 207 (1996), all of which are incorporated by reference). Other analog nucleic acids include those with positive backbones (Dempcy, R. O. et al., *Proc. Natl. Acad. Sci. USA* 92:6097-101 (1995)); non-ionic backbones (U.S. Pat. Nos. 5,386,023; 5,637,684; 5,602, 240; 5,216,141; and 4,469,863; Kiedrowski et al., *Angew. Chem. Intl. Ed. English* 30:423 (1991); Letsinger, R. L. et al., *J. Am. Chem. Soc.* 110: 4470 (1988); Letsinger, R. L. et al., *Nucleoside & Nucleotide* 13: 1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4: 395 (1994); Jeffs et al., *J. Biomolecular NMR* 34:17 (1994)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., *Chem. Soc. Rev.* 169-176 (1995)); all references are hereby expressly incorporated by reference.

Telomeric nucleic acids, or a target nucleic acid, may be any length, with the understanding that longer sequences are more specific. In some embodiments, it may be desirable to fragment or cleave the sample nucleic acid into fragments of 100-10,000 base pairs, with fragments of roughly 500 base-pairs being preferred in some embodiments. Fragmentation or cleavage may be done in any number of ways well known to those skilled in the art, including mechanical, chemical, and enzymatic methods. Thus, the nucleic acids may be subjected to sonication, French press, shearing, or treated with nucleases (e.g., DNase, restriction enzymes, RNase etc.), or chemical cleavage agents (e.g., acid/piperidine, hydrazine/piperidine, iron-EDTA complexes, 1,10-phenanthroline-copper complexes, etc.).

The samples containing telomere and target nuclei acids may be prepared using well-known techniques. For instance, the sample may be treated using detergents, sonication, electroporation, denaturants, etc., to disrupt the cells. The target nucleic acids may be purified as needed. Components of the reaction may be added simultaneously, or sequentially, in any order as outlined below. In addition, a variety of agents may be added to the reaction to facilitate optimal hybridization, amplification, and detection. These include salts, buffers, neutral proteins, detergents, etc. Other agents may be added to improve efficiency of the reaction, such as protease inhibitors, nuclease inhibitors, anti-microbial agents, etc., depending on the sample preparation methods and purity of the target nucleic acid. When the telomere nucleic acid is in the form of RNA, these nucleic acids may be converted to DNA, for example by treatment with reverse transcriptase (e.g., MoMuLV reverse transcriptase, Tth reverse transcriptase, etc.), as is well known in the art.

Numerous methods are available for determining telomere length. In one embodiment, telomere length is determined by measuring the mean length of a terminal restriction fragment (TRF). The TRF is defined as the length—in general the average length-of fragments resulting from complete digestion of genomic DNA with a restriction enzyme that does not cleave the nucleic acid within the telomeric sequence. Typically, the DNA is digested with restriction enzymes that cleaves frequently within genomic DNA but does not cleave within telomere sequences. Typically, the restriction enzymes have a four base recognition sequence (e.g., AluI, HinfI, RsaI, and Sau3A1) and are used either alone or in combination. The resulting terminal restriction fragment contains both telomeric repeats and subtelomeric DNA. As used herein, subtelomeric DNA are DNA sequences adjacent to tandem repeats of telomeric sequences and contain telomere repeat sequences interspersed with variable telomeric-like sequences. The digested DNA is separated by electrophoresis and blotted onto a support, such as a membrane. The fragments containing telomere sequences are detected by hybridizing a probe, i.e., labeled repeat sequences, to the membrane. Upon visualization of the telomere containing fragments, the mean lengths of terminal restriction fragments can be calculated (Harley, C. B. et al., *Nature*. 345(6274):458-60 (1990), hereby incorporated by reference). TRF estimation by Southern blotting gives a distribution of telomere length in the cells or tissue, and thus the mean telomere length of all cells.

For the various methods described herein, a variety of hybridization conditions may be used, including high, moderate, and low stringency conditions (see, e.g., Sambrook, J. *Molecular Cloning: A Laboratory Manual*, 3rd Ed., Cold Spring Harbor Laboratory Press, Cold Spring Harbor, N.Y. (2001); Ausubel, F. M. et al., *Current Protocols in Molecular Biology*, John Wiley & Sons (updates to 2002); hereby incorporated by reference). Stringency conditions are sequence-dependent and will be different in different circumstances, including the length of probe or primer, number of mismatches, G/C content, and ionic strength. A guide to hybridization of nucleic acids is provided in Tijssen, P. "Overview of Princples of Hybridization and the Strategy of Nucleic Acid Assays," in *Laboratory Techniques in Biochemistry and Molecular Biology: Hybridization with Nucleic Acid Probes*, Vol 24, Elsevier Publishers, Amsterdam (1993). Generally, stringent conditions are selected to be about 5-10° C. lower than the thermal melting point (i.e., $T_m$) for a specific hybrid at a defined temperature under a defined solution condition at which 50% of the probe or primer is hybridized to the target nucleic acid at equilibrium. Since the degree of stringency is generally determined by the difference in the hybridization temperature and the $T_m$, a particular degree of stringency may be maintained despite changes in solution condition of hybridization as long as the difference in temperature from $T_m$ is maintained. The hybridization conditions may also vary with the type of nucleic acid backbone, for example ribonucleic acid or peptide nucleic acid backbone.

In another embodiment, telomere length is measured by quantitative fluorescent in situ hybridization (Q-FISH). In this method, cells are fixed and hybridized with a probe conjugated to a fluorescent label, for example, Cy-3, fluoresceine, rhodamine, etc. Probes for this method are oligonucleotides designed to hybridize specifically to telomere sequences. Generally, the probes are 8 or more nucleotides in length, preferably 12-20 more nucleotides in length. In one aspect, the probes are oligonucleotides comprising naturally occurring nucleotides. In a preferred embodiment, the probe is a peptide nucleic acid, which has a higher $T_m$, than analogous natural sequences, and thus permits use of more stringent hybridization conditions. Generally, cells are treated with an agent, such as colcemid, to induce cell cycle arrest at metaphase provide metaphase chromosomes for hybridization and analysis. Digital images of intact metaphase chromosomes are acquired and the fluorescence intensity of probes hybridized to telomeres quantitated. This permits measurement of telomere length of individual chromosomes, in addition to average telomere length in a cell, and avoids problems associated with the presence of subtelomeric DNA (Zjilmans, J. M. et al., *Proc. Natl. Acad Sci. USA* 94:7423-7428 (1997); Blasco, M. A. et al., *Cell* 91:25-34 (1997); incorporated by reference).

In another embodiment, telomere lengths are measured by flow cytometry (Hultdin, M. et al., *Nucleic Acids Res.* 26: 3651-3656 (1998); Rufer, N. et al., *Nat. Biotechnol.* 16:743-747 (1998); incorporated herein by reference). Flow cytometry methods are variations of FISH techniques. If the starting material is tissue, a cell suspension is made, generally by mechanical separation and/or treatment with proteases. Cells are fixed with a fixative and hybridized with a telomere sequence specific probe, preferably a PNA probe, labeled with a fluorescent label. Following hybridization, cell are washed and then analyzed by FACS. Fluorescence signal is measured for cells in $G_0/G_1$ following appropriate subtraction for background fluorescence. This technique is suitable for rapid estimation of telomere length for large numbers of samples. Similar to TRF, telemere length is the average length of telomeres within the cell.

In a preferred embodiment, telomere lengths are determined by assessing the average telomere length using polymerase chain reaction (PCR). Procedures for PCR are widely used and well known (see for example, U.S. Pat. Nos. 4,683, 195 and 4,683,202). In brief, a target nucleic acid is incubated in the presence of primers, which hybridizes to the target nucleic acid. When the target nucleic acid is double stranded, they are first denatured to generate a first single strand and a second single strand so as to allow hybridization of the primers. Any number of denaturation techniques may be used, such as temperature, although pH changes, denaturants, and other techniques may be applied as appropriate to the nature of the double stranded nucleic acid. A DNA polymerase is used to extend the hybridized primer, thus generating a new copy of the target nucleic acid. The synthesized duplex is denatured and the hybridization and extension steps repeated. Carrying out the amplification in the presence of a single primer results in amplification of the target nucleic acid in a linear manner. For the purposes of the present invention, linear amplification using a single primer is encompassed within the meaning of PCR. By reiterating the steps of denaturation, annealing, and extension in the presence of a second primer that hybridizes to the complementary target strand, the target nucleic acid encompassed by the two primers is amplified exponentially.

By "primer", "primer nucleic acid", "oligonucleotide primer", "oligonucleotide probe" or grammatical equivalents as used herein is meant a nucleic acid that will hybridize to some portion of the target nucleic acid. The primers or probes of the present invention are designed to be substantially complementary to a target sequence such that hybridization of the target sequence and the primers of the present invention occurs, and proper 3' base pairing allows primer extension to take place. Such complementarity need not be perfect. Thus, by "complementary" or "substantially complementary" herein is meant that the probes are sufficiently complementary to the target sequences to hybridize under normal reaction conditions. Deviations from perfect complementary are permissible so long as deviations are not sufficient to completely preclude hybridization. However, if the number of alterations or mutations is sufficient such that no hybridization can occur under the least stringent of hybridization conditions, as defined below, the sequence is not a complementary target sequence.

Although primers are generally single stranded, the nucleic acids as described herein may be single stranded or double stranded, as specified, or contain portions of both double stranded or single stranded sequence. The nucleic acid may be DNA, RNA, or hybrid, where the nucleic acid contains any combination of deoxyribo- and ribonucleotides, and any combination of bases, including uracil, adenine, thymine, cytosine, guanine, xanthine hypoxanthine, isocytosine, isoguanine, inosine, etc., although generally occurring bases are preferred. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred herein as a nucleotide.

The size of the primer nucleic acid may vary, as will be appreciated by those in the art, in general varying from 5 to 500 nucleotides in length, with primers of between 10 and 100 being preferred, between 12 and 75 being particularly preferred, and from 15 to 50 being especially preferred, depending on the use, required specificity, and the amplification technique.

For any primer pair, the ability of the primers to hybridize to each other may be examined by aligning the sequence of the first primer to the second primer. The stability of the hybrids, especially the thermal melting temperature ($T_m$), may be determined by the methods described below and by methods well known in the art. These include, but are not limited to, nearest-neighbor thermodynamic calculations (Breslauer, T. et al., *Proc. Natl. Acad. Sci. USA* 83:8893-97 (1986); Wetmur, J. G., *Crit. Rev. Biochem. Mol. Biol.* 26:227-59 (1991); Rychlik, W. et al., *J. NIH Res.* 6:78 (1994)), Wallace Rule estimations (Suggs, S. V. et al "Use of Synthetic oligodeoxribonucleotides for the isolation of specific cloned DNA sequences," *Developmental biology using purified genes*, D. B. Brown, ed., pp 683-693, Academic Press, New York (1981), and $T_m$ estimations based on Bolton and McCarthy (see Baldino, F. J. et al., *Methods Enzymol.* 168: 761-77 (1989); Sambrook, J. et al., *Molecular Cloning: A Laboratory Manual*, Chapter 10, Cold Spring Harbor Laboratory Press, Cold Spring Harbor, N.Y., (2001)). All references are hereby expressly incorporated by reference. The effect of various parameters, including, but not limited to, ionic strength, probe length, G/C content, and mismatches are taken into consideration when assessing hybrid stability. Consideration of these factors are well known to those skilled in the art (see, e.g., Sambrook, J., supra).

In a preferred embodiment, the primers of the present invention are designed to have similar $T_m$s. As used herein, primers with similar $T_m$s have a $T_m$ difference of about 10° C. or less, preferably 5° C. or less, and more preferably 2° C. or less. Use of primer sets (e.g., primer pairs) with similar or identical $T_m$s allow use of an annealing/extension temperature optimal for both primers and provides similar amplification efficiency at a particular amplification condition. Advantages are the ability to use similar concentrations of primers, particularly at lower concentrations, which limits generation of unwanted amplification products. By comparison, when $T_m$s of the primers are dissimilar, one primer is used at a higher concentration to compensate for differences in amplification efficiency. This higher primer concentration results in undesirable amplification products at a lower number of PCR cycles.

In one aspect, primers with similar $T_m$s are made by altering the length of primers or by selecting primers having similar guanosine-cytosine (GC) content. $T_m$s are assessed by the methods described above. As used herein, a "similar GC content" is meant a primer set which has a GC content difference of about 10% or less, more preferably a difference of about 5% or less, and most preferably a difference of about 2% or less, such that the primers display similar $T_m$s, as given above. In the primer design process, $T_m$ and/or GC content are initially assessed for the region that hybridizes to the target nucleic acid. For primers with a non-hybridizing 5' terminal region described above, additional analysis of the $T_m$ and GC content is conducted for the entire primer sequence. Generally, primers are designed to have higher similarities of GC content at the 3' terminal region since it is this region that is extended by the polymerase.

The primers of the present invention may be used to amplify various target nucleic acids. A single primer set, for example a primer pair, may be used to amplify a single target nucleic acid. In another embodiment, multiple primer sets may be used to amplify a plurality of target nucleic acids. Amplifications may be conducted separately for each unique primer set, or in a single reaction vessel using combinations of primer sets, generally known in the art as multiplexing. When multiple primer sets are used in a single reaction, primers are designed to limit formation of undesirable products and limit interference between primers of each primer set.

In one embodiment of a PCR based technique for measuring telomere length, the method involves digesting genomic DNA with a restriction enzyme to generate a DNA fragment containing the subtelomeric and telomeric region. An oligonucleotide in the form of a linker is covalently attached to the telomere end of the DNA fragment. Hybridization of a primer complementary to the linker followed by primer extension with a polymerase results in an extension product encompassing the subtelomeric and telomeric region. Use of a second primer specific to the subtelomeric region allows for amplification of a product defined by the region between the two primers (see, e.g., U.S. Pat. No. 5,834,193; incorporated by reference). In one aspect, the genomic DNA is treated with a single stranded specific nuclease to generate blunt ends, which allows efficient ligation of a double stranded linker onto the end of the telomere region. Subsequent amplification will provide a representative measure of telomere length even though treatment with nuclease will remove the 3' single stranded region present at the end of the telomere.

In a variation on the primer extension method, an oligonucleotide primer specific to the subtelomeric region is used to prime copying of the telomeric and the subtelomeric region without attaching a linker to the telomere end. Repeated rounds of hybridization, extension and denaturation results in linear amplification of the subtelomeric/telomeric region. The amplified product may be detected by using labeled primers in the amplification reaction or by hybridizing a labeled probe to the amplified product.

Another method for determining telomere length by PCR involves use of telomere specific primers designed to amplify the tandem repetitive telomere sequences (Cawthon, R. M. Nucleic Acids Res. 30: e47 (2002); WO 03/064615; incorporated by reference). This method involves uses of primers substantially complementary to telomere repeats but which do not undergo self-priming when the primers hybridize to each other during the PCR reaction. Amplification by this PCR technique results in direct amplification of telomere sequences, which when quantitated, provides a measure of the average telomere length.

As used herein, a "repetitive unit", "repeat unit", "repetitive element" is meant a minimal nucleotide sequence which is reiterated or repeated in the repetitive region, such as a telomere repeat sequence. In the present invention, the repetitive unit for amplification may comprise repetitive units of 1 or more nucleotides, more preferably repetitive units between 3 and 100 nucleotides, and most preferably repetitive units between 4 and 30 nucleotides. In general, these repetitive units are arranged in tandem fashion, although there may be non-repetitive nucleotides present between the repetitive units. By a "plurality" of repetitive elements herein is meant at least two or more repetitive units in the repetitive region. The number of repetitive units amplified for each set of primers will depend on the length of the primer and the nucleotide length of the repetitive unit. As will be appreciated by those skilled in the art, primer sequences and primer lengths may be chosen based on stability and specificity of the primer for the repetitive units.

Generally, the primers for direct amplification of telomere repeats comprises a first primer which hybridizes to a first single strand of the target nucleic acid and a second primer which hybridizes to a second single strand of the target nucleic acid, where the first and second strands are substantially complementary. The primers are capable of primer extension by polymerase when hybridized to their respective strands. That is, the primers hybridized to the target nucleic acid have their 3' terminal nucleotide residues complementary to the nucleotide residue on the target nucleic acid such that the primers are extendable by polymerase. The selected primers are complementary to repetitive units of the repetitive region. In one aspect, at least one nucleotide residue of at least one of the primers is altered to produce mismatches with a nucleotide residue of at least one repetitive unit to which the primer hybridizes, wherein the altered nucleotide residue also produces a mismatch with the 3' terminal nucleotide residue of the other primer when the primers hybridize to each other. The inclusion of a mismatch prevents or limits primer extension of primer-primer hybrids.

In one preferred embodiment, at least one nucleotide residue of the first primer is altered to produce a mismatch between the altered residue and a nucleotide residue of at least one repetitive unit of the first strand to which the primer hybridizes, wherein the altered nucleotide residue also produces a mismatch with the 3' terminal nucleotide residue of the second primer when the first and second primers hybridize to each other.

The altered nucleotide residue is preferably at least 1 nucleotide residue, more preferably at least 2 nucleotide residues, and most preferably at least 3 nucleotide residues from the 3' terminal nucleotide to allow efficient extension by polymerase when the altered primer hybridizes to target nucleic acids.

In another aspect, both primers used for directly amplifying repetitive units comprise at least one altered nucleotide residue such that hybridization of primers to each other generates mismatches between the altered residues and the 3' terminal residues of both primers. Thus, in a preferred embodiment, in addition to the altered nucleotide residue on the first primer described above, at least one nucleotide residue of the second primer is altered to produce a mismatch between the altered residue and a nucleotide residue of at least one repetitive unit of the second strand to which the second primer hybridizes, wherein the altered residue on the second primer also produces a mismatch with the 3' terminal nucleotide of the first primer when the primers hybridize to each other.

In yet another embodiment for amplifying repetitive units of a repetitive region, the present invention comprises a first primer which hybridizes to more than one repetitive unit on a first single strand of a target nucleic acid, and a second primer which hybridizes to more than one repetitive unit on a second single strand of the target nucleic acid, where the first and second strands are substantially complementary. The primers are capable of primer extension when hybridized to their respective strands of the target nucleic acid, as described above. In one aspect, nucleotide residues of at least one of the primers are altered to produce mismatches between the altered residues and the nucleotide residues at the identical nucleotide position of each repetitive unit of the single strand of the target nucleic acid to which the primer hybridizes. These altered nucleotide residues also produce mismatches with the 3' terminal nucleotide residue of the other primer when the primers hybridize to each other, thus further limiting primer-extension of primer-primer hybrids.

Accordingly, in one preferred embodiment, nucleotide residues of the first primer are altered to produce mismatches between the altered residues and nucleotide residues at the identical nucleotide position of each repetitive unit of the first strand of the target nucleic acid to which the primer hybridizes. These altered nucleotides also produce mismatches with the 3' terminal nucleotide residue of the second primer when first second primer hybridizes to each other.

The altered nucleotide residues are preferably at least 1 nucleotide residue, more preferably at least 2 nucleotide residues, and most preferably at least 3 nucleotide residues from the 3' terminal nucleotide to allow efficient extension by polymerase when the altered primer hybridizes to target nucleic acids.

In another aspect, both primers comprise altered nucleotide residues such that hybridization of primers to each other results in mismatches of the 3' terminal nucleotide of both primers. Thus, in a preferred embodiment, in addition to the altered nucleotide residues on the first primer, nucleotide residues on the second primer are altered to produce mismatches between the altered residues of the second primer and nucleotide residues at the identical nucleotide position of each repetitive unit of the second strand to which the primer hybridizes. These altered nucleotides of the second primer also produce mismatches with the 3' terminal nucleotide residue of the first primer when the primers hybridize to each other.

Since primers hybridized to target nucleic acids must be capable of primer extension, alterations of the first and second primers must be on non-complementary nucleotides of the repetitive unit. Thus, in one aspect, when both the first and second primers comprise altered residues, the alterations are at adjacent nucleotide positions of the repetitive unit. In another aspect, the alterations are situated on non-adjacent nucleotide positions of the repetitive unit. In general, mismatches at adjacent nucleotide positions provide for the most number of base paired or complementary residues between the altered nucleotide and the 3' terminal nucleotide, which may be important for efficiently amplifying short repetitive sequences (i.e., 3-6 basepairs).

In another embodiment, the first and second primers further comprise a 5' terminal region that does not hybridize (i.e., basepair) with the target nucleic acid. The unpaired region comprises one or more nucleotides, with a preferred range of 3 to 60 nucleotides, and a most preferred range of 4 to 30 nucleotides. When the primers are directed towards amplification of repetitive units of a repetitive region, the 5' unpaired region blocks the 3' ends of the replicated primer extension products from initiating nucleic acid synthesis from the internal repetitive units of the amplification products during subsequent amplification cycles.

Although the 5'-terminal unpaired region may be of any sequence which does not hybridize to the target nucleic acid, in a preferred embodiment, the unpaired region comprises restriction sites, unique sequences for purposes of sequencing or primer extension reactions (i.e., amplification), or tag sequences for detecting and measuring the amplified product.

As discussed above, in a preferred embodiment, the primers of the present invention are designed to have similar $T_m$s to limit generation of undesirable amplification products and to permit amplification and detection of several target nucleic acids in a single reaction volume. In addition, since the telomeres of various organisms have differing repetitive unit sequences, amplifying telomeres of a specific organism will employ primers specific to the repetitive unit of each different organism. Human telomeric sequences are used herein to illustrate practice of the present invention for direct amplification and quantitation of tandemly repeated nucleic acid sequences, but is not limited to the disclosed specific embodiment.

Amplification reactions are carried out according to procedures well known in the art, as discussed above (see, e.g., U.S. Pat. Nos. 4,683,195 and 4,683,202). The time and temperature of the primer extension step will depend on the polymerase, length of target nucleic acid being amplified, and primer sequence employed for the amplification. The number of reiterative steps required to sufficiently amplify the target nucleic acid will depend on the efficiency of amplification for each cycle and the starting copy number of the target nucleic acid. As is well known in the art, these parameters can be adjusted by the skilled artisan to effectuate a desired level of amplification. Those skilled in the art will understand that the present invention is not limited by variations in times, temperatures, buffer conditions, and the amplification cycles applied in the amplification process.

In hybridizing the primers to the target nucleic acids and in the amplification reactions, the assays are generally done under stringency conditions that allow formation of the hybrids in the presence of target nucleic acid. Those skilled in the art can alter the parameters of temperature, salt concentration, pH, organic solvent, chaotropic agents, or other variables to control the stringency of hybridization and also minimize hybridization of primers to non-specific targets (i.e., by use of "hot start" PCR or "touchdown" PCR).

Following contacting the primers to the target nucleic acids, the reaction is treated with an amplification enzyme, generally a polymerase. A variety of suitable polymerases are well known in the art, including Taq polymerase, KlenTaq, Tfl polymerase, DynaZyme etc. Generally, although all polymerases are applicable to the present invention, preferred polymerases are thermostable polymerases lacking 3' to 5' exonuclease activity since use of polymerases with strong 3' to 5' exonuclease activity tends to remove the mismatched 3' terminal nucleotides. Also useful are polymerases engineered to have reduced or non-functional 3' to 5' exonuclease activities (e.g., Pfu(exo-), Vent(exo-), Pyra(exo-), etc.). Also applicable are mixtures of polymerases used to optimally extend hybridized primers. In another aspect, polymerase enzymes useful for the present invention are formulated to become active only at temperatures suitable for amplification. Presence of polymerase inhibiting antibodies, which become inactivated at amplification temperatures, or sequestering the enzymes in a form rendering it unavailable until amplification temperatures are reached, are all suitable. These polymerase formulations allow mixing all components while preventing priming of non-target nucleic acid sequences.

In another aspect, those skilled in the art will appreciate that various agents may be added to the reaction to increase processivity of the polymerase, stabilize the polymerase from inactivation, decrease non-specific hybridization of the primers, or increase efficiency of replication. Such additives include, but are not limited to, dimethyl sulfoxide, formamide, acetamide, glycerol, polyethylene glycol, or proteinacious agents such as *E. coli*. single stranded DNA binding protein, T4 gene 32 protein, bovine serum albumin, gelatin etc. In another aspect, the person skilled in the art can use various nucleotide analogs for amplification of particular types of sequences, for example GC rich or repeating sequences. These analogs include $c^7$-dGTP, hydroxymethyl-dUTP, dITP, 7-deaza-dGTP etc.

The products of the amplification are detected and analyzed by methods well known to those skilled in the art. Amplified products may be analyzed following separation and/or purification of the products, or by direct measurement of product formed in the amplification reaction. Separation and purification methods include, among others, electrophoresis (i.e., agarose or acrylamide gels), chromatography (i.e., affinity, molecular sieve, reverse phase etc.) and hybridization. The purified products may be subjected to further amplifications as is well known in the art. For detection, the product may be identified indirectly with fluorescent compounds, for example with ethidium bromide or SYBR™Green or by hybridization with labeled nucleic acid probes. Alternatively, labeled primers or labeled nucleotides are used in the amplification reaction to label the amplification product. The label comprises any detectable moiety, including fluorescent labels, radioactive labels, electronic labels, and indirect labels such as biotin or digoxigenin. When indirect labels are used, a secondary binding agent that binds the indirect label is used to detect the presence of the amplification product. These secondary binding agents may comprise antibodies, haptens, or other binding partners (e.g., avidin) that bind to the indirect labels. Secondary binding agents are preferably labeled with fluorescent moieties, radioactive moieties, enzymes etc.

In one embodiment, the amplification product may be detected and quantitated during the amplification reaction by real time quantitative PCR, variations of which are well known in the art. For instance, the TaqMan system uses a probe primer which hybridizes to sequences in an internal sequence within the nucleic acid segment encompassed by the primers used to amplify the target nucleic acid (Heid, C. A. et al., Genome Res. 6:986-94 (1996); Holland, P. M. et al., *Proc. Natl. Acad. Sci. USA* 88: 7276-80 (1991)). This probe is labeled with two different fluorescent dyes (i.e., dual-labeled flurogenic oligonucleotide probe), the 5' terminus reporter dye (TAMRA) and the 3' terminus fluorescence quenching dye (FAM). Cleavage of the probe by the 5' to 3' exonuclease activity of DNA polymerase during the extension phase of PCR releases the flurogenic molecule from proximity of the quencher, thus resulting in increased fluorescence intensity.

In another aspect, real time quantitative PCR may be based on fluorescence resonance energy transfer (FRET) between hybridization probes (Wittwer, C. T., Biotechniques 22:130-138 (1997)). In this method, two oligonucleotide probes hybridize to adjacent regions of the target nucleic acid sequence. The upstream probe is labeled at the 3' terminus with an excitor dye (i.e., FITC) while the adjacently hybridizing downstream probe is labeled at the 5' terminus with a reporter dye. Hybridization of the two probes to the amplified target nucleic acid sequences positions the two dyes in close spatial proximity sufficient for FRET to occur. This allows monitoring the quantity of amplified product during the polymerase chain reaction. A similar approach is used in the molecular beacon probes (Tyagi, S., *Nat. Biotechnol.* 16: 49-53 (1998)). Molecular beacons are oligonucleotide probes comprising a quencher dye and a reporter dye at the opposite ends of the PCR product specific oligonucleotide. The dyes may also function based on FRET, and therefore may also be comprised of an excitation dye and a reporter dye. Short complementary segments at the 5' and 3' terminal regions allow for formation of a stem-loop structure, which positions the dyes at the terminal ends of the oligonucleotide into close proximity, thus resulting in fluorescence quenching or FRET. When the oligonucleotide hybridizes to a PCR product through complementary sequences in the internal region of the molecular beacon probe, fluorescence of the oligonucleotide probe is affected, thus allowing monitoring of product synthesis.

In a preferred embodiment, real time quantitative PCR may use fluorescent dyes that preferentially bind to double stranded nucleic acid amplification products during the PCR reaction to permit continuous monitoring of product synthesis (see, e.g., Higuchi, R. et al., *Biotechnology* 11: 1026-30 (1993); T. B. et al., *Biotechniques* 24: 954-62 (1998)). Suitable fluorescent dyes include, among others, ethidium bromide, YO PRO-1™ (Ishiguro, T., *Anal. Biochem.* 229: 207-13 (1995)), and SYBR™ Green dyes (Molecular Probes, Eugene, Oreg., USA). When amplifying target nucleic acids comprising repetitive regions, FRET or molecular beacon based probes are not preferred if FRET or molecular beacon probes are directed to repetitive units since they will hybridize to repetitive sequences on the primers, thereby failing to distinguish between primers and amplified product.

In a further preferred embodiment, real time quantitative PCR is accomplished with primers containing a single fluorophore attached near the 3' terminal nucleotide (Nazarenko, I. et al., *Nucleic Acids Res.* 30: e37 (2002); Nazarenko, I. et al., *Nucleic Acids Res.* 30: 2089-2195 (2002); LUX™ Fluorogenic Primers, Invitrogen, Palo Alto, Calif.; hereby incorporated by reference). The 5' end of these primers have a 5 to 7 nucleotide extension capable of hybridizing to the 3' terminal region to generate a blunt-ended hairpin (i.e., stem-loop) structure, whose formation results in fluorescence quenching of the fluorophore. When the primer forms a duplex, for example by primer extension on a template, the quenching is reduced or eliminated, thus providing a measure of PCR product in the sample. Because only a single flurophore is used, different fluorophores may be used and detected in a single reaction. Consequently, these primers are useful for amplification and detection of a plurality of different target nucleic acids in a single reaction vessel by use of different primer sets with distinguishable fluorophores. As discussed herein, various target nucleic acids include combinations of single copy genes and repetitive sequences, as further described herein.

Instrumentation suitable for real time monitoring of PCR reactions is available for use in quantitative PCR methods (ABI Prism 7700, Applied Biosystems Division, Perkin Elmer, Fosters City, Calif., USA; LightCycler™, Roche Molecular Biochemicals, Indianapolis, Ind., USA). Other real time PCR detection systems are known to those of ordinary skill in the art.

When real time quantitative PCR is used to detect and measure the amplification products, various algorithms are used to calculate the number of target nucleic acids in the samples (see, e.g., ABI Prism 7700 Software Version 1.7; Lightcycler™ Software Version 3). Quantitation may involve use of standard samples with known copy number of the target nucleic acid, and generation of standard curves from the logarithms of the standards and the cycle of threshold ($C_t$). In general, $C_t$ is the PCR cycle or fractional PCR cycle where the fluorescence generated by the amplification product is several deviations above the baseline fluorescence (Higuchi, R. et al., supra). Real time quantitative PCR provides a linearity of about 7 to 8 orders of magnitude, which allows measurement of the copy number of target nucleic acids over a wide dynamic range. The absolute number of target nucleic acid copies can be derived from comparing the $C_t$ values of the standard curve and the samples.

The copy number of telomere repeats or target nucleic acid may also be determined by comparative quantitative real time PCR. Use of nucleic acids of known copy number or consistent copy number allows quantitation of the copy number of target nucleic acids in a sample. The standard may be a single copy gene, a nucleic acid of known copy number, or when quantitating RNA copy number, a constitutively expressed housekeeping gene (see Johnson, M. R. *Anal. Biochem.* 278: 175-84 (2000); Boulay, J.-L., et al., Biotechniques 27: 228-32 (1999)).

The amplified products are quantitated as described above. In a preferred embodiment, real time quantitative PCR is used to determine the copy number of the telomere repetitive units in the target nucleic acid sample. Standards for determining and comparing telomere repetitive unit number include use of single copy genes (e.g., ribosomal phosphoprotein 364B) or a target nucleic acid of known copy number (e.g., a plasmid with known number of telomere repetitive units). By the methods described herein, the copy number of repetitive units of a large number of samples may be quantitated for purposes of determining the number of telomere repetitive units, and thus the average length of telomeres.

Following determination of telomere length for an individual or population, the measured values may correlated with mortality risk or disease occurrence for a population, and in particular, individuals within a population. A variety of statistical analysis may be used for this purpose, including, but not limited to, Cox proportional hazard regression analysis, Kaplan-Meier survival distribution estimate, Peto Wilcoxon test, maximum likelihood analysis, multiple regression analysis, and others. Such statistical methods, including various forms of survival analysis, are well known in the art and described in standard works on statistics (see, e.g., Cantor, A. B. *SAS Survival Analysis Techniques for Medical Research*, 2nd Ed., SAS Publishing, Cary, N.C. (2003); Hosmer, D. W. et al., *Applied Survival Analysis: Regression Modeling of Time to Event Data* Wiley-Interscience, Hoboken, N.J. (2002); Lee, E. T., Statistical Methods for Survival Data Analysis, 2nd Ed., John Wiley & Sons, Hoboken, N.J. (1992); and Schork, M. A. and Remington, R. D., Statistics with Applications to the Biological and Health Sciences, 3rd Ed., Prentice Hall, Upper Saddle River, N.J. (2000). All publications are incorporated by reference in their entirety.

In the present invention, the telomere length, or in some embodiments, rates of changes in telomere length, is correlated with mortality risk. Thus, the telomere length is a useful marker for predicting survival or mortality risk for different age groups. In a further embodiment, the measured telomere length is used for correlating occurrence of diseases, particularly age related diseases, including, but not limited to cardiovascular disease (e.g., hypertension, myocardial infarction, stroke, etc.), neoplastic diseases (e.g., cancers, carcinomas, malignant tumors, etc.), and susceptibility to infectious diseases.

The correlations between telomere length and mortality risk or disease occurrence may be used for disease prognosis and therapeutic applications. In one preferred embodiment, the method is used to identify individuals or groups of individuals with telomeres lengths falling within the ranges of those populations with increased mortality risk, advanced biological age, or increased risk for death from age related diseases. This may provide a basis for identifying individuals who may warrant additional medical screening or early medical intervention.

For example, it is shown herein that there is a statistically significant increased mortality rate ratio for death from infectious disease for those in the bottom half for telomere length compared to those in the top half for telomere length. In addition, a statistically significant increase in mortality rate ratio for death from heart disease is observed for those in the bottom half vs. those in the top half for telomere length. Thus, in clinical practice, the telomere length assay results may help physicians in assessing each specific patient's risk of these diseases, and so may make a difference in the physician's treatment plan for the patient.

In another application, the method may be used to identify environmental factors affecting or related to telomere shortening. Populations with heightened exposure to carcinogens, teratogens, radiation, or other environmental factors may be tested and examined for the existence of any statistically significant correlations between exposure, telomere length, and age related diseases. This may identify environmental risk factors which can be reduced or minimized to decrease adverse effect on the health of populations.

In a further application, the methods of the present invention may be used to identify genes, genetic linkages, or other genetic factors contributing to telomere shortening and their relation to mortality and susceptibility to various age related disease. Studies of large populations can facilitate identification of such risk factors.

The foregoing descriptions of specific embodiments of the present invention have been presented for purposes of illustration and description. They are not intended to be exhaustive or to limit the invention to the precise forms disclosed, and obviously many modifications and variations are possible in light of the above teachings.

All publications and patent applications mentioned in this specification are herein incorporated by reference to the same extent as if each individual publication or patent application was specifically and individually indicated to be incorporated by reference.

EXAMPLES

Example 1

Determining Average Telomere Length

Genomic DNA was extracted from blood samples by standard procedures. The samples used to compare quantitative PCR vs. Southern blot approaches to telomere measurement were donated by 21 unrelated individuals (11 women and 10 men, age range 61-94 years) from Utah families that are part of the Centre pour les Etudes du Polymorphisme Humaine (CEPH) collection used worldwide for building the human genetic linkage map (White, R. et al. (1985) Nature 313: 101-105). Purified DNA samples were diluted in 96-well microtiter source plates to approximately 1.75 ng/ul in 10 mM Tris-HCl, 0.1 mM EDTA, pH 7.5 (final volume 300 ul per well), heated to 95° C. for 5 minutes in a thermal cycler, quick-chilled by transfer to an ice-water bath for 5 minutes, centrifuged briefly at 700×g, sealed with adhesive aluminum foil, and stored at 4° C. until the time of assay.

Real time quantitative PCR on the extracted DNA samples are performed on separate 96 well plates. Two master mixes of PCR reagents were prepared, one with the telomere (T) primer pair, the other with the single copy gene (S) primer pair. Thirty microliters of T master mix was added to each sample well and standard curve well of the first plate, and 30 microliters of S master mix was added to each sample well and standard curve well of the second plate. For each individual in whom the T/S ratio was assayed, three identical 20 ul aliquots of the DNA sample (35 ng per aliquot) were added to plate 1, and another three aliquots were added to the same well positions in plate 2. For each standard curve, one standard DNA sample was diluted serially in TE (10 mM Tris, 1 mM EDTA, pH 7.0) by −1.68-fold per dilution to produce five concentrations of DNA ranging from 0.63 ng/ul up to 5 ng/ul, which were then distributed in 20 ul aliquots to the standard curve wells on each plate. The plates were then sealed with a transparent adhesive cover, centrifuged briefly at 700×g, and stored at 4° C. in the dark until the PCR was performed (0-3 days later).

The final concentrations of reagents in PCR with tel 1 and tel 2 primers were 150 nM 6-ROX and 0.2×SYBR™ Green I (Molecular Probes, Inc.); 15 mM Tris-HCl, pH 8.0; 50 mM KCl; 2 mM $MgCl_2$; 0.2 mM of each dNTP; 5 mM DTT; 1% DMSO; and 1.25 units of AmpliTaq Gold DNA polymerase (Applied Biosystems, Inc.). The thermal cycling profile began with a 95° C. incubation for 10 min. to activate the AmpliTaq Gold DNA polymerase. With tel 1 and tel 2 primers, there followed 18 cycles of 95° C.×15 s, 54° C.×2 min. Telomere primer concentrations were tel 1, 270 nM; tel 2, 900 nM. The primer sequences in 5' to 3' direction were tel 1, GGTTTTTGAGGGTGAGGGTGAGGGTGAGGGTGAGGGT; (SEQ ID NO:1) and tel 2, TCCCGACTATCCCTATCCCTATCCCTATCCCTATCCCTA (SEQ ID NO:2).

Alternatively, the primer used for amplifying the telomere repeat sequences were optimized to have similar $T_m$s, particularly by designing the primers to have similar or identical GC content: tel 1b, CGGTTTGTTTGGGTTTGGGTTTGG-GTTTGGGTTTGGGTT (SEQ ID NO:6); and tel 2b, GGCT-TGCCTTACCCTTACCCTTACCCTTACCCTTACCCT (SEQ ID NO:7). Each of the $T_m$ optimized primers has perfect complementarity to telomere DNA sequences in the last five bases at the 3' end of the primer. As with tel 1 and tel 2 primers, the optimized primers have a purposefully introduced single base substitution at the sixth base from the 3' end and at every sixth base thereafter in the 5' direction, for a total of five introduced base changes. This results in five single base mismatches when the primer is optimally hybridized to telomeric DNA. Hybridization of the optimized primers to each other results in base pairing at four out of the six positions in the repeat and where the 3' terminal base of each primer is mismatched relative to the other primer.

For amplifications using tel 1b and tel 2b, the amplifications conditions were 0.4×Sybr Green I, 1.5 mM $MgCl_2$, 1% DMSO, 2.5 mM DTT, 200 micromolar each dNTP, 0.75 Units of AmpliTaq Gold DNA polymerase, 450 nM of tel 1b primer, and 450 nM of tel 2b primer, in a final volume of 30 microliters per reaction. The thermal cycling profile was 95° C.×10 min. to activate the polymerase; followed by 18 cycles of 95° C. for 15 sec. (denaturation) and 56° C. for 2 min. (anneal/extend). No ROX dye is needed for this assay.

For PCR with single copy gene 36B4 primers, reactions conditions were 150 nM 6-ROX and 0.2×SYBR™ Green I (Molecular Probes, Inc.); 15 mM Tris-HCl, pH 8.0; 50 mM KCl; 2 mM $MgCl_2$; 0.2 mM of each dNTP; 5 mM DTT; 1% DMSO; and 1.25 units of AmpliTaq Gold DNA polymerase (Applied Biosystems, Inc.). The final 36B4 (single copy gene) primer concentrations were 36B4u, 300 nM and 36B4d, 500 nM. The thermal cycling profile began with a 95° C. incubation for 10 min. to activate the AmpliTaq Gold DNA polymerase. Subsequently, there followed 30 cycles of 95° C.×15 s, 58° C.×1 min. Alternatively, the amplification conditions were 0.4×Sybr Green I, 3.5 mM $MgCl_2$, 1% DMSO, 2.5 mM DTT, 200 micromolar each dNTP, 0.75 Units of AmpliTaq Gold DNA polymerase, 300 nM of 36B4u primer, and 500 nM of 36B4d primer, in a final volume of 30 microliters per reaction. The thermal cycling profile was 95° C.×10 min. to activate the polymerase; followed by 30 cycles of 95° C. for 15 sec. (denaturation) and 56° C. for 1 min. (anneal/extend). No ROX dye is needed for this assay. Sequences of the single copy gene primers are 36B4u, CAGCAAGTGG-GAAGGTGTAATCC (SEQ ID NO:8); and 36B4d, CCCAT-TCTATCATCAACGGGTACAA (SEQ ID NO:9). (The 36B4 gene, which encodes acidic ribosomal phosphoprotein PO, is located on chromosome 12; see Boulay et al. (1999) Biotechniques 27: 228-32).

All PCRs were performed on ABI Prism 7700 Sequence Detection System (Applied Biosytems, Inc., Foster City, Calif., USA), a thermal cycler equipped to excite and read emissions from fluorescent molecules during each cycle of the PCR. ABI's SDS version 1.7 software was then used to generate the standard curve for each plate and to determine the dilution factors of standard corresponding to the T and S amounts in each sample.

In the presence of 35 ng of human DNA, a telomere PCR product was detectable by real time quantitative PCR beginning from about 9 cycles of PCR. Analysis of the product after 25 cycles by electrophoresis on agarose gels and staining with ethidium bromide shows a smear of products beginning from about 76 base pairs, which is equivalent to the sum of the lengths of the telomere specific primers, to products of about 400 base pairs. The copy number of the PCR is proportional to the number of sites available for binding of the primer in the first cycle of the PCR. Omitting the genomic DNA results in no detectable amplification product after 25 cycles for either the telomere or single copy gene primers.

Mean telomere restriction fragment (TRF) lengths were determined as described by Slagboom et al. (1994) Am. J. Hum. Genet 55: 876-82. Approximately 0.5 ug of purified whole blood DNA was digested to completion with Hae III restriction enzyme. Digested samples were then mixed with DNA size standards, separated by electrophoresis on agarose gels, and transferred to a nylon membrane. The membranes were hybridized with $^{32}P$ end labeled oligonucleotide, $(TTAGGG)_7$ (SEQ ID NO:10), washed to remove non-specifically bound probe, exposed to a phosphor plate for 1 to 5 days, and scanned with a PhosphorImager (Molecular Dynamics, Inc.). Blots were then stripped of the telomere probe, hybridized with radiolabeled probe for the DNA size standards, washed, exposed to a phosphor plate, and scanned. The size standard images and telomere smear images were then superimposed to locate the positions of the size intervals within the telomere smears. Mean TRF length was then calculated as mean TRF length=$(S\ OD_i)/(S\ OD_i/L_i)$, where $OD_i$ is total radioactivity above background in interval i, and $L_i$ is the average length of i in basepairs. This entire procedure was performed twice; i.e., the two mean TRF length values determined on each individual were obtained from two independent experiments.

To measure the T/S value (telomere to single copy gene ratio), the $C_t$ value—the fractional cycle number at which the amplification sample's accumulating fluorescence crosses a set threshold value that is several standard deviations above background fluorescence—was determined for samples amplified with telomere specific (T) primers and single copy gene specific (S) primers. Since the amount of PCR product approximately doubles in each cycle of the PCR, the T/S ratio is approximately $[2^{Ct(telomeres)}/2^{Ct(single\ copy\ gene)}]^{-1} = 2^{-\Delta Ct}$. The average $\Delta C_t$ was −9.05 (see FIG. 2). That is, PCR of a single copy gene required about 9 more cycles than PCR of telomeres to produce equivalent fluorescent signal as measured by real time PCR. The standard deviation was 1.48%.

The relative T/S ratio, which is the T/S of one sample relative to the T/S of another sample, is expressed as $2^{-(\Delta Ct1-\Delta Ct2)}=2^{-\Delta\Delta Ct}$. This formula allows calculating the relative T/S ratio of each sample. DNA samples of 21 unrelated patients were amplified and quantitated by real time quantitative PCR (see Experiment 2). Comparison of the relative T/S ratio calculated from PCR correlated well with the mean TRF lengths determined by Southern hybridization (see FIG. 3). The y intercept is about 3.6 kbp, which is approximately the mean length of the subtelomeric region between the restriction enzyme recognition sites and the beginning of the telomeric hexamer repeats (Hultdin, M. (1998) Nucleic Acids. Res. 26: 3651-56). Moreover, the observed average telomere length in whole blood as measured by relative T/S ratio varies over a 2.5 range among unrelated age and sex-matched adults. This range of variability is in excellent agreement with other studies on the range of variation of TRF lengths in age matched adults if the average subtelomeric length of 3.4 kbp is subtracted from each reported mean TRF length (Hultdin, M. (1998) Nucleic Acids Res. 3651-56; Vaziri, H. et al. (1993) Am. J. Hum. Genet. 52: 661-67).

Example 2

Telomere Length and Mortality in Humans

The 143 research subjects were unrelated Utah residents aged 60-97 years, who donated blood from 1982-1986 to contribute to the CEPH (Centre d'Etude du Polymorphisme Humain) collection of cell lines used to build the human genetic linkage map (White R. et al, Nature 313: 101-105 (1985)) and for whom follow-up survival data were available. Birth and death dates were obtained from the Utah Population Database (UPDB), and from the Social Security Death Index. There were 101 known deaths by mid-2002. For the remaining 42 subjects, date at which they were last known to be alive was established post blood draw. The survival analysis by cause of death (from Utah death certificates coded to the International Classification of Diseases, 9th and 10th revisions) was restricted to the 124 individuals with UPDB identification numbers. This study was approved by the University of Utah's Institutional Review Board.

Relative TLs in total genomic DNA prepared directly from the original blood draws were measured by a quantitative polymerase chain reaction assay (Cawthon, R. M. Nucleic Acids Res. 30: e47 (2002)), which determines the relative ratio of telomere repeat copy number to single copy gene copy number (T/S ratio) in experimental samples as compared to a reference DNA sample. In another set of DNA samples T/S ratios were measured relative to the same reference DNA sample, and mean terminal restriction fragment (TRF) lengths were determined (Cawthon, supra). The slope of the plot of mean TRF length vs. T/S for these samples served as the conversion factor for calculating approximate telomere lengths in basepairs for each T/S ratio in this survival study. In these subjects aged 60-97 years, TL ranged from 1930-4310 bp. Each one year increase in age at blood draw was associated with a 0.0048 decrease in the relative T/S ratio (95% CI [0.00137 to 0.00823], P=0.0074), corresponding to about 14 bp of telomere sequence lost per year. Women and men did not differ significantly in the rate of telomere shortening estimated from these cross-sectional data (P=0.645). Women's telomeres were 3.5% longer than those of men after adjusting for age, but this difference was not statistically significant (P=0.157).

Cox proportional hazard regression models (Ghali, W. A. et al. JAMA 286: 1494-1497 (2001)) were used to test whether differences in telomere length (TL) among statistically age-matched individuals were associated with differences in survival. TL, when analyzed as a continuous variable, was inversely associated with the age-adjusted mortality rate (Cox proportional hazards regression coefficient=−1.87, 95% CI [−3.35 to -0.392], P=0.013). In all other analyses TL was treated as a dichotomous trait ("shorter" vs. "longer"), using all available samples in each comparison (i.e., bottom half of the TL distribution vs. top half, and bottom 25% vs. top 75%). Because older individuals tend to have shorter telomeres than younger individuals, the use of a single TL distribution for the entire sample would result in a higher proportion of older than younger subjects being scored as "shorter" for TL, and a higher proportion of younger than older subjects being scored as "longer" for TL. To achieve more balanced proportions of subjects with "shorter" vs. "longer" TLs at every age, the sample was stratified into six categories of age at draw (60-64 years, number of subjects: n=19; 65-69, n=37; 70-74, n=37; 75-79, n=29; 80-84, n=12; and 85+, n=9), and the TL distribution was determined independently within each category. Individuals in the bottom half for TL in each age group were pooled together, and their survival was compared to that of the pooled top half individuals. Similarly, individuals in the bottom quartile for TL in each age group were pooled, and their survival was compared to that of the pooled top 75% individuals. There was no significant difference in the mean age at draw between the compared groups (i.e., bottom vs. top half, bottom 25% vs. top 75%). Survival was assessed beginning with the time at blood draw, except as noted. Cox models were used to control for variation in mortality rate due to age differences, both between the age at blood draw categories, and within each age group.

Individuals with shorter telomeres had a mortality rate nearly twice that of individuals with longer telomeres (Table 1). The loss in median survival associated with shorter telomeres (FIG. 1) was 4.8 years for women, and 4.0 years for men (averaged across all age-at-blood-draw categories). TL was a significant predictor of mortality when measured from ages 60 to 74 (P=0.021), and a moderate predictor when measured from age 75 onward (P=0.086) (Table 1, FIG. 2). Excess mortality risks associated with short vs. long telomeres did not vary by sex (P=0.878), age at blood draw (P=0.946), or time since blood draw (P=0.851). The excess mortality rates of those in the bottom half of TL remained significant even when only those subjects surviving at least 5 years after the blood draw were included in the analysis (P=0.0063, n=112).

TABLE 1

Mortality rate ratios associated with having short vs. long telomeres in whole blood DNA

| | Mortality rate ratio | 95% Confidence interval | P value |
|---|---|---|---|
| All-cause mortality | | | |
| Both sexes combined (n = 143, d = 101) | 1.86 | (1.22–2.83) | 0.004 |
| Women (n = 71, d = 46) | 2.16 | (1.07–4.39) | 0.033 |
| Men (n = 72, d = 55) | 1.94 | (1.01–3.74) | 0.047 |
| Age at draw <75 (n = 93, d = 53) | 1.96 | (1.11–3.48) | 0.021 |
| Age at draw ≥75 (n = 50, d = 48) | 1.73 | (0.93–3.24) | 0.086 |
| Cause-specific mortality | | | |
| Heart (n = 124, d = 30) | 3.18 | (1.36–7.45) | 0.008 |
| Cerebrovascular (n = 124, d = 15) | 1.35 | (0.36–5.13) | 0.660 |
| Cancer (n = 124, d = 12) | 1.43 | (0.34–6.03) | 0.625 |
| Infectious (n = 124, d = 8) | 8.54 | (1.52–47.9) | 0.015 |
| Other known (n = 124, d = 16) | 2.15 | (0.71–6.50) | 0.174 |
| All known causes except heart + infectious (n = 124, d = 43) | 1.70 | (0.82–3.53) | 0.156 |

Each mortality rate ratio (MMR) presented here is the ratio of the death rate for subjects with shorter telomeres to the death rate for subjects with longer telomeres. In all five categories of all-cause mortality, and in the first category of cause-specific mortality (heart disease), the MMR reported above is for individuals from the bottom half of the telomere length (TL) distribution vs. those from the top half of the distribution. In the remaining five categories of cause-specific mortality, the MMR reported is for individuals from the bottom 25% of the TL distribution vs. those from the top 75% of the distribution. n: total number of individuals in each analysis. d: for all-cause mortality, the number of deceased individuals in each analysis; for cause-specific mortality, the number of individuals in each analysis who died from the listed cause of death.

The rate ratios for cause-specific mortality associated with having shorter vs. longer telomeres are also presented in Table 1. Subjects from the bottom half of the TL distribution had a heart disease mortality rate that was over three times that of subjects from the top half. This elevated risk of dying from heart disease remained significant even when the analysis was limited to subjects who survived at least five years after the blood draw (number of heart disease deaths=21, mortality rate ratio 4.87, 95% CI [1.59 to 14.9], P=0.006).

Mortality rates for cerebrovascular disease and cancer were also higher in individuals with shorter telomeres, although not significantly higher. The mortality rate from infectious disease was eight times higher for individuals in the bottom 25% of the TL distribution than for individuals in the top 75%, a statistically significant difference. Among the infectious disease deaths, the shortest time between the blood draw and death was 1.5 years. The remaining 16 deaths due to known causes, other than those mentioned above, were treated as a single category of mortality; the risk of dying in this category was also higher in individuals with shorter telomeres, although not significantly higher.

What is claimed:

1. A method for determining mortality risk of a human, said method comprising:
   a) determining telomere length in total genomic DNA prepared from a somatic cell of said human; and
   b) comparing said telomere length with somatic cell telomere length in an age-matched population of the human, wherein a human having a shorter telomere length compared to the age-matched control is a human with an increased mortality risk,-wherein said mortality risk is associated with vascular disease;
   wherein the average telomere length is determined by polymerase chain reaction using a first primer pair to amplify telomere repeat sequences and a second primer pair to amplify a target nucleic acid that is a single copy gene; and
   wherein the first primer pair consists of tel 1b (SEQ ID NO: 6) and tel 2b (SEQ ID NO: 7).

2. The method according to claim 1, wherein telomere length is the average telomere length.

3. The method according to claim 1, wherein said telomere length is determined from blood.

4. The method according to claim 1, wherein said telomere length is determined from lymphoid cells.

5. The method according to claim 4, wherein said lymphoid cells comprise T cells.

6. The method according to claim 1, wherein said aged matched population is within about 10 human years of the age of said organism.

7. The method according to claim 6, wherein said aged matched population is within about 5 years of the age of said human.

8. The method of claim 1, wherein the single copy gene is the 36B4 gene encoding acidic ribosomal phosphoprotein PO.

9. The method of claim 8, wherein second primer pair to amplify a single copy gene consists of 36B4u (SEQ ID NO: 8) and 36B4d (SEQ ID NO: 9).

10. A method for determining mortality risk of a human, said method comprising:
   a) determining the rate of telomere length decrease in total genomic DNA prepared from in a somatic cell of said human; and
   b) comparing said rate of decrease with rate of telomere length decrease in the somatic cells of an age-matched population of the human, wherein a human having a higher rate of telomere length decrease compared to the age-matched control is a human with an increased mortality risk, wherein said mortality risk is associated with vascular disease;
   wherein the rate of teleomere length decrease is determined by polymerase chain reaction using a first primer pair to amplify telomere repeat sequences and a second primer pair to amplify a single copy gene; and wherein the first primer pair consists of tel 1b (SEQ ID NO: 6) and tel 2b (SEQ ID NO: 7).

* * * * *

SEQUENCE LISTING

```
<160> NUMBER OF SEQ ID NOS: 10

<210> SEQ ID NO 1
<211> LENGTH: 37
<212> TYPE: DNA
<213> ORGANISM: Artificial
<220> FEATURE:
<223> OTHER INFORMATION: Synthetic

<400> SEQUENCE: 1
ggtttttgag ggtgagggtg agggtgaggg tgagggt                              37

<210> SEQ ID NO 2
<211> LENGTH: 39
<212> TYPE: DNA
<213> ORGANISM: Artificial
<220> FEATURE:
<223> OTHER INFORMATION: Synthetic

<400> SEQUENCE: 2
tcccgactat ccctatccct atccctatcc ctatccta                             39

<210> SEQ ID NO 3
<211> LENGTH: 90
<212> TYPE: DNA
<213> ORGANISM: Homo sapiens

<400> SEQUENCE: 3
ccctaaccct aaccctaacc ctaaccctaa ccctaaccct aaccctaacc ctaaccctaa     60
ccctaaccct aaccctaacc ctaaccctaa                                     90

<210> SEQ ID NO 4
<211> LENGTH: 90
<212> TYPE: DNA
<213> ORGANISM: Homo sapiens

<400> SEQUENCE: 4
ttagggttag ggttagggtt agggttaggg ttagggttag ggttagggtt agggttaggg    60
ttagggttag ggttagggtt agggttaggg                                     90

<210> SEQ ID NO 5
<211> LENGTH: 6
<212> TYPE: DNA
<213> ORGANISM: Homo sapiens

<400> SEQUENCE: 5 ttaggg                                                                6

<210> SEQ ID NO 6
<211> LENGTH: 39
<212> TYPE: DNA
<213> ORGANISM: Artificial
<220> FEATURE:
<223> OTHER INFORMATION: Synthetic

<400> SEQUENCE: 6
cggtttgttt gggtttgggt ttgggtttgg gtttgggtt                           39
```

```
<210> SEQ ID NO 7
<211> LENGTH: 39
<212> TYPE: DNA
<213> ORGANISM: Artificial
<220> FEATURE:
<223> OTHER INFORMATION: Synthetic

<400> SEQUENCE: 7
ggcttgcctt acccttaccc ttacccttac ccttaccct                              39

<210> SEQ ID NO 8
<211> LENGTH: 23
<212> TYPE: DNA
<213> ORGANISM: Artificial
<220> FEATURE:
<223> OTHER INFORMATION: Synthetic

<400> SEQUENCE: 8
cagcaagtgg gaaggtgtaa tcc                                               23

<210> SEQ ID NO 9
<211> LENGTH: 25
<212> TYPE: DNA
<213> ORGANISM: Artificial
<220> FEATURE:
<223> OTHER INFORMATION: Synthetic

<400> SEQUENCE: 9
cccattctat catcaacggg tacaa                                             25

<210> SEQ ID NO 10
<211> LENGTH: 42
<212> TYPE: DNA
<213> ORGANISM: Artificial
<220> FEATURE:
<223> OTHER INFORMATION: Synthetic

<400> SEQUENCE: 10
ttagggttag ggttagggtt agggttaggg ttagggttag gg                          42
```